(12) United States Patent
Stephanopoulos et al.

(10) Patent No.: US 11,708,594 B2
(45) Date of Patent: Jul. 25, 2023

(54) RECONFIGURABLE DNA NANO-TWEEZER

(71) Applicant: Arizona Board of Regents on behalf of Arizona State University, Scottsdale, AZ (US)

(72) Inventors: Nicholas Stephanopoulos, Scottsdale, AZ (US); Minghui Liu, Chandler, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 774 days.

(21) Appl. No.: 16/653,235

(22) Filed: Oct. 15, 2019

(65) Prior Publication Data
US 2020/0140911 A1    May 7, 2020

Related U.S. Application Data

(60) Provisional application No. 62/746,139, filed on Oct. 16, 2018.

(51) Int. Cl.
| | |
|---|---|
| *C12P 19/34* | (2006.01) |
| *C12N 15/11* | (2006.01) |
| *B82Y 40/00* | (2011.01) |
| *B82Y 5/00* | (2011.01) |

(52) U.S. Cl.
CPC ............ *C12P 19/34* (2013.01); *C12N 15/111* (2013.01); *B82Y 5/00* (2013.01); *B82Y 40/00* (2013.01); *C12N 2310/122* (2013.01); *C12N 2310/3181* (2013.01); *C12N 2310/531* (2013.01)

(58) Field of Classification Search
CPC ............ C12N 15/113; C12N 2310/122; C12N 2310/531; C12P 19/34; C12Q 1/6818; C12Q 2523/319; C12Q 2525/301
USPC .... 435/6.1, 91.1, 91.31, 455, 458; 536/23.1, 536/24.5
See application file for complete search history.

(56) References Cited

U.S. PATENT DOCUMENTS

2018/0016569 A1    1/2018  Fu

FOREIGN PATENT DOCUMENTS

WO    2018187687    10/2018

OTHER PUBLICATIONS

Liu et al (Nat. Commun., vol. 4, 2127 (2013)) (Year: 2013).*
Zhang et al (Nature Chemistry, vol. 3, pp. 103-113 (2011)) (Year: 2011).*
Of Kamiya et al (Accounts of Chemical Research, vol. 47, No. 6, pp. 1663-1672 (2014)) (Year: 2014).*
Asanuma, H., et al. "Photoregulation of the formation and dissociation of a DNA duplex by using the cis-trans isomerization of azobenzene." Angewandte Chemie International Edition 38.16 (1999): 2393-2395.
Bruns, C. J., et al. "Rotaxane-based molecular muscles." Accounts of chemical research 47.7 (2014): 2186-2199.
Buff, M. et al. "Light-Activatable Nucleic Acids' Caged'at the Nucleobases." CHIMIA International Journal for Chemistry 63.5 (2009): 261-264.
Deiters, A. "Light activation as a method of regulating and studying gene expression." Current opinion in chemical biology 13.5-6 (2009): 678-686.
Douglas, S., et al. Erratum: Self-assembly of DNA into nanoscale three-dimensional shapes. Nature 459, 1154 (2009).
Douglas, S. M., et al. "A logic-gated nanorobot for targeted transport of molecular payloads." Science 335.6070 (2012): 831-834.
Doye, JPK, et al. "Coarse-graining DNA for simulations of DNA nanotechnology." Physical Chemistry Chemical Physics 15.47 (2013): 20395-20414.
Fields, A.P. et al. Euler buckling and nonlinear kinking of doublestranded DNA, 2013, Nucleic acids research, 41 (21):9881-9890.
Fu, J., et al. "Multi-enzyme complexes on DNA scaffolds capable of substrate channelling with an artificial swinging arm." Nature nanotechnology 9.7 (2014): 531.
Funke, J. J., et al. "Placing molecules with Bohr radius resolution using DNA origami." Nature nanotechnology 11.1 (2016): 47-52.
Funke, J. J., et al. "Uncovering the forces between nucleosomes using DNA origami." Science advances 2.11 (2016): e1600974.
Goddard, N. L., et al. "Sequence dependent rigidity of single stranded DNA." Physical review letters 85.11 (2000): 2400.
Harrison, RM et al. Coarse-grained modelling of strong DNA bending i: Thermodynamics and comparison to an experimental "molecular vice", 2015 arXiv preprint arXiv:1506. 09005.
Hong, F, et al. "DNA origami: scaffolds for creating higher order structures." Chemical reviews 117.20 (2017): 12584-12640.
Huang, F, et al. "DNA branch migration reactions through photocontrollable toehold formation." Journal of the American Chemical Society 135.21 (2013): 7967-7973.
Kamiya, Y. et al. "Light-driven DNA nanomachine with a photoresponsive molecular engine." Accounts of chemical research 47.6 (2014): 1663-1672.

(Continued)

*Primary Examiner* — Jane J Zara
(74) *Attorney, Agent, or Firm* — Quarles & Brady LLP

(57) ABSTRACT

A photocaged DNA nano-tweezer and methods of using said photocaged DNA nano-tweezer are described. In particular, provided herein is a DNA nano-tweezer comprising a hairpin with a single-stranded loop that comprises a first arm and a second arm; and a trigger strand complementary to the single-stranded loop and comprising at least one photocaged residue with a protecting group.

14 Claims, 21 Drawing Sheets
(21 of 21 Drawing Sheet(s) Filed in Color)
Specification includes a Sequence Listing.

(56) References Cited

OTHER PUBLICATIONS

Ke, Y., et al. "Three-dimensional structures self-assembled from DNA bricks." science 338.6111 (2012): 1177-1183.

Le, J. V., et al. "Probing nucleosome stability with a DNA origami nanocaliper." ACS nano 10.7 (2016): 7073-7084.

Li, S., et al. "A DNA nanorobot functions as a cancer therapeutic in response to a molecular trigger in vivo." Nature biotechnology 36.3 (2018): 258.

List, J., et al. "Long-range movement of large mechanically interlocked DNA nanostructures." Nature communications 7.1 (2016): 1-7.

Liu, M., et al. "A DNA tweezer-actuated enzyme nanoreactor." Nature communications 4.1 (2013): 1-5.

Lo, P K, et al. "Loading and selective release of cargo in DNA nanotubes with longitudinal variation." Nature chemistry 2.4 (2010): 319.

Lusic, H., et al. "A new photocaging group for aromatic N-heterocycles." Synthesis 2006.13 (2006): 2147-2150.

Lusic, H., et al. "Photochemical DNA activation." Organic letters 9.10 (2007): 1903-1906.

Marras, A. E., et al. "Programmable motion of DNA origami mechanisms." Proceedings of the National Academy of Sciences 112.3 (2015): 713-718.

Pirrung, MC et al. "Photoremoveable protecting groups in DNA synthesis and microarray fabrication," Chapter 6 of Dynamic Studies in Biology: Phototriggers, Photoswitches and Caged Biomolecules, 2005.

Powell, J. T., et al. "DNA origami rotaxanes: tailored synthesis and controlled structure switching." Angewandte Chemie 128.38 (2016): 11584-11588.

Rothemund, PWK, et al. "Design and characterization of programmable DNA nanotubes." Journal of the American Chemical Society 126.50 (2004): 16344-16352.

Rothemund, PWK. "Folding DNA to create nanoscale shapes and patterns." Nature 440.7082 (2006): 297-302.

Samanta, S, et al. "Photoswitching azo compounds in vivo with red light." Journal of the American Chemical Society 135.26 (2013): 9777-9784.

Sulc, P, et al. "Sequence-dependent thermodynamics of a coarse-grained DNA model." The Journal of chemical physics 137.13 (2012): 135101.

U.S. Appl. No. 16/603,338, filed Oct. 7, 2019, Green et al.

U.S. Appl. No. 16/816,029, filed Mar. 11, 2020, Stephanopoulos et al.

Vologodskii, A et al. "Strong bending of the DNA double helix." Nucleic acids research 41.14 (2013): 6785-6792.

Walbert, S., et al. "Photolabile protecting groups for nucleosides: Mechanistic studies of the 2-(2-nitrophenyl) ethyl group." Helvetica Chimica Acta 84.6 (2001): 1601-1611.

Wang, X. et al. "Defining single molecular forces required to activate integrin and notch signaling." Science 340.6135 (2013): 991-994.

Wei, B. et al. "Complex shapes self-assembled from single-stranded DNA tiles." Nature 485.7400 (2012): 623-626.

Winfree, E., et al. "Design and self-assembly of two-dimensional DNA crystals." Nature 394.6693 (1998): 539-544.

Yan, H., et al. "DNA-templated self-assembly of protein arrays and highly conductive nanowires." science 301.5641 (2003): 1882-1884.

Zhang, DY, et al. "Dynamic DNA nanotechnology using strand-displacement reactions." Nature chemistry 3.2 (2011): 103.

Zheng, J, et al. "From molecular to macroscopic via the rational design of a self-assembled 3D DNA crystal." Nature 461.7260 (2009): 74-77.

Zhou, C., et al. "Reversible regulation of protein binding affinity by a DNA machine." Journal of the American Chemical Society 134.3 (2012): 1416-1418.

* cited by examiner

FIGS. 2A-2C CONTINUED
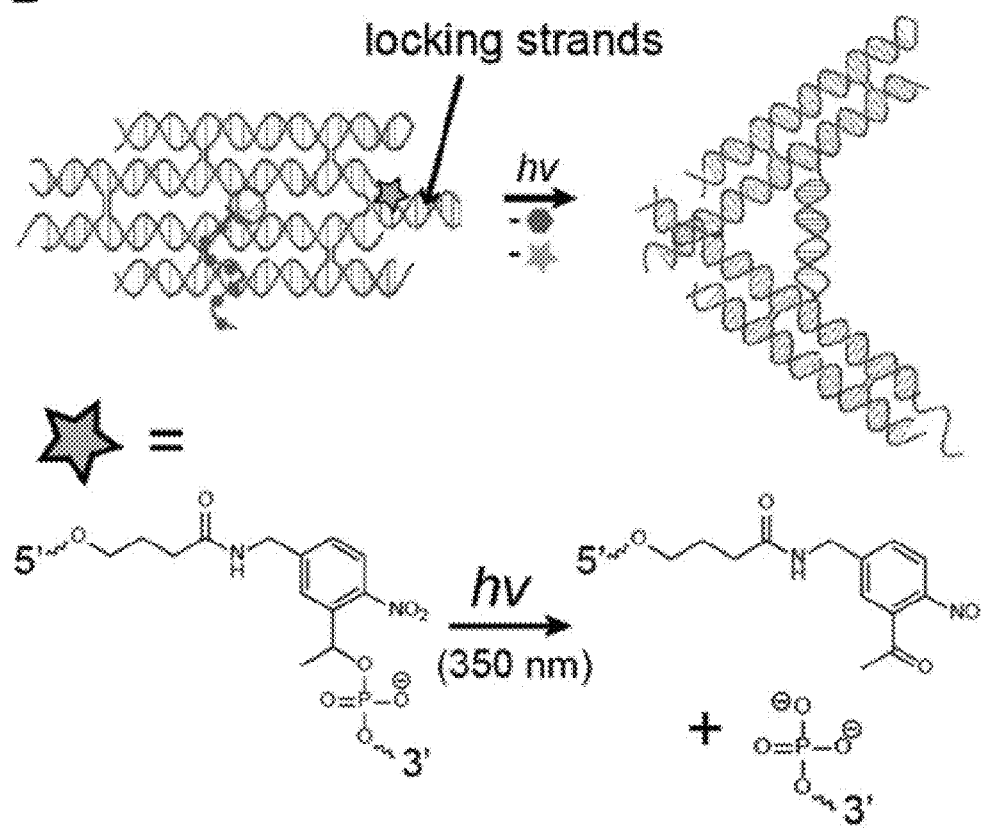
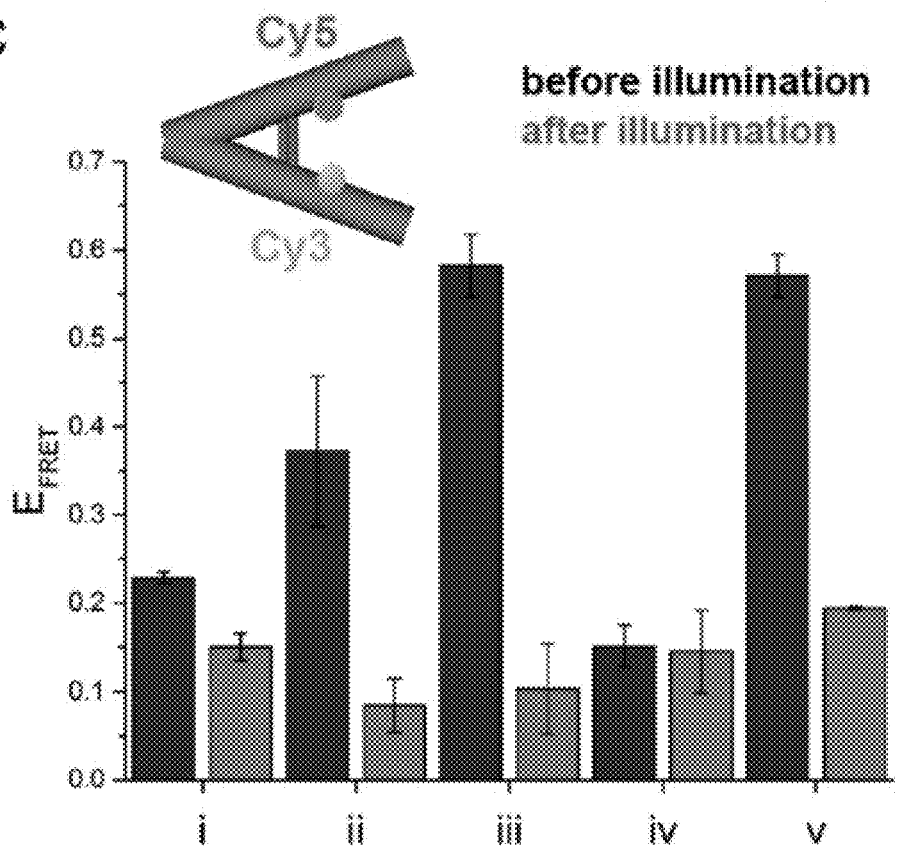

RECONFIGURABLE DNA NANO-TWEEZER

CROSS-REFERENCE TO RELATED APPLICATIONS

This application claims priority to U.S. Provisional Application No. 62/746,139, filed Oct. 16, 2018, which is incorporated herein in its entirety.

STATEMENT REGARDING FEDERALLY SPONSORED RESEARCH

This invention was made with government support under FA9550-17-1-0053 awarded by the Air Force Office of Scientific Research (AFOSR). The government has certain rights in the invention.

REFERENCE TO A SEQUENCE LISTING SUBMITTED VIA EFS-WEB

The content of the ASCII text file of the sequence listing named "112624_01126_ST25.txt" which is 10.4 kb in size was created on Oct. 14, 2019 and electronically submitted via EFS-Web herewith the application is incorporated herein by reference in its entirety.

BACKGROUND

One of the central goals of nanotechnology is to build machines, switches, or reconfigurable devices at the nanoscale level that can operate in a stimulus-responsive manner. These constructs would have applications in studying receptor-ligand interactions (Wang et al. 2013), releasing cargo for drug delivery (Douglas et al. 2012), or constructing dynamic materials such as artificial muscles (Bruns et al. 2014). DNA is highly promising molecular building block for creating such systems owing to the exquisite programmability of Watson-Crick pairing, allowing for simple assemblies based on just a few strands (Lo et al. 2010, Rothemund et al. 2004, Winfree et al. 1998, Yan et al. 2003, Zheng et al. 2009) or highly complex and anisotropic structures using techniques like DNA origami (Douglas et al. 2009, Hong et al. 2017, Rothemund et al. 2006) or 3D bricks (Ke et al. 2012, Wei et al. 2012). In recent years, a whole suite of nanoscale analogues of macroscopic mechanical elements and devices have been reported, including hinges/calipers (Funke et al. 2016), pistons (Marras et al. 2015) boxes with addressable latches (Douglas et al. 2012, Jiang et al. 2018) or interlocked rotaxane nanostructures (List et al. 2016, Powell et al. 2016). By far the most common way to actuate these constructs is through the addition of single-stranded nucleotides that can reconfigure the structure through toehold-mediated strand displacement (Zhang et al. 2011) whereby an oligonucleotide outcompetes a shorter strand in order to break and replace a DNA hybridization interaction. Despite the ability to programmably and orthogonally control multiple elements through specific trigger strands, this approach has the disadvantage that the strand must be added externally, limiting its use in applications such as inside of cells, or in vivo, and often in high molar excess to achieve suitable kinetics.

SUMMARY

In a first aspect, described herein is a DNA nano-tweezer comprising a hairpin with a single-stranded loop that comprises a first arm and a second arm and a trigger strand complementary to the single-stranded loop and comprising at least one photocaged residue with a protecting group. In some embodiments, the single-stranded loop is a poly-A loop the trigger strand is a poly-T strand. In some embodiments, the single-stranded loop is a poly-C loop and the trigger strand is a poly-G loop. In some embodiments, the single-stranded loop and the trigger strand are selected from the group consisting of a poly-A loop, a poly-T loop, a poly-G loop, and a poly-C loop.

In some embodiments, the protecting group is a 6-nitropiperonyloxymethyl protecting group. In some embodiments, the DNA nano-tweezer additionally comprises a locking strand. In some embodiments, the locking strand comprises an o-nitrobenzyl ester photocleavable backbone.

In some embodiments, the DNA nano-tweezer additionally comprising at least one fluorescent label. In some embodiments, the DNA nano-tweezer additionally comprising a ligand.

In some embodiments, the distance between the first arm and the second arm is between about 1 nm and about 10 nm. The distance between the first arm and the second is measured between the distal end of the first arm away from the hinge and the distal end of the second arm away from the hinge, as demonstrated in FIG. 1A.

In a second aspect, provided herein is a method of inducing a conformational change in nanostructured DNA, the method comprising the step of exposing a DNA nano-tweezer as described herein to a pulse of light, whereby the DNA nano-tweezer undergoes a conformational change from a closed conformation to an open conformation. In some embodiments, the protecting group is a 6-nitropiperonyloxymethyl protecting group and the light is UV light.

In some embodiments, the light have a wavelength between about 300 nm and about 400 nm. In some embodiments, the pulse of light is between about 1 second and about 10 seconds.

In a third aspect, described herein is a DNA nano-tweezer comprising a hairpin with a single-stranded loop, wherein the loop has at least two arms with a distance of between about 4 nm to about 18 nm between the at least two arms, and a trigger strand complementary to the single-stranded loop and comprising at least one photocaged residue, wherein the DNA nano-tweezer is in a closed conformation until exposed to a pulse of light whereby the photocaged residue is released and the trigger strand is hybridized to the single-stranded loop forming an open conformation wherein the distance between the at least two arms is at least 18 nm. In some embodiments, the single-stranded loop and the trigger strand are selected from the group consisting of a poly-A loop, a poly-T loop, a poly-G loop, and a poly-C loop.

In some embodiments, the photocaged residue comprises a 6-nitropiperonyloxymethyl protecting group. In some embodiments, the DNA nano-tweezer additionally comprising a ligand. In some embodiments, the DNA nano-tweezer additionally comprising a fluorescent label.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

DETAILED DESCRIPTION

A reconfigurable DNA nano-tweezer is disclosed herein that can be switched between a closed and open state with a pulse of light. In its initial state, the tweezer is held shut using a hairpin with a single-stranded loop. Also incorporated in the structure is a trigger strand that is complementary to the single-stranded loop and includes photocaged residues. Upon illumination with a given wavelength of light, the cages are released and the trigger strand hybridizes to the hairpin loop, opening the tweezer and increasing the distance between its arms. This intramolecular process is roughly 60 times faster than adding an external trigger strand, and provides a mechanism for the rapid interconversion of DNA nanostructures with light.

The DNA nano-tweezer structures comprising photocaged residues as described herein are useful for studying receptor-ligand interactions, releasing cargo for drug delivery, or constructing dynamic materials, such as artificial muscles. For example, photocaged DNA nano-tweezers may be used to assemble light-activated nano-robots and spring-loaded mechanical assemblies, and to achieve on-demand cargo release from a targeted nano-cage.

As used herein, "photocaged DNA nano-tweezer," refers to a DNA nano-tweezer which has a trigger strand that includes at least one photocaged residue, the trigger strand being incorporated into the structure of the DNA nano-tweezer as opposed to being an external trigger strand added separately. Upon exposure to a pulse of light, the photocages are released from the trigger stand and the trigger strand hybridizes to the single-stranded hairpin loop inducing a change in the DNA tweezer from the closed conformation to the open conformation.

Figure 1A:
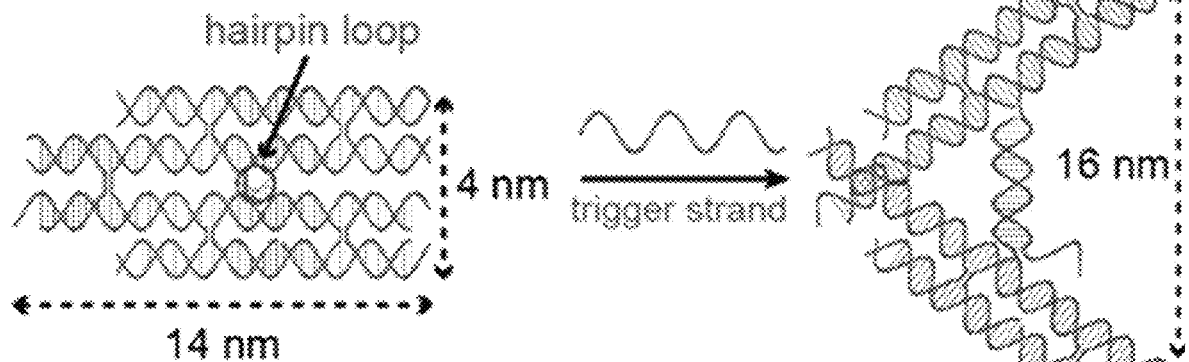
FIGS. 1A-1E show the design of photocaged tweezers and characterization of photocaged strands. A) Design and dimensions of original tweezer, which requires an external trigger strand (blue) to open hairpin loop (red). B) Design of photocaged tweezer with internally incorporated trigger strand (blue). (hv—high frequency light) C) UV/Vis spectra of photocage deprotection. D) Denaturing PAGE gel characterization of photocage deprotection: lane M, ssDNA ladder (nt); lane 1, non-protected control strand; lane 2, photocaged strand; lane 3, photocaged strand after deprotection. E) Native PAGE gel characterization of photocage deprotection: lane M, dsDNA ladder (bp); lane 1, non-protected control strand; lane 2, control strand bound with a complementary polyA strand; lane 3, mixture of photocaged trigger strand and poly(A) mimic of hairpin strand; lane 4, sample in lane 3 after deprotection.

As used herein, "DNA nano-tweezer" refers to a nanoscale structure including a hairpin with a single-stranded loop and a first arm and a second arm linked by a crossover hinge wherein the distance between the tip of the first arm and the tip of the second arm is reversibly or irreversibly controlled by binding and release of a trigger strand to the single-stranded loop of the hairpin. The trigger strand may be attached to either the first arm or the second arm and typically has a free end unattached to the DNA nano-tweezer. Alternatively, the trigger strand can be external to the DNA nano-tweezer. It will be readily understood by one of ordinary skill in the art that the flexibility and size of the DNA nano-tweezer may be manipulated by changing the size and sequences of DNA used in constructing the DNA nano-tweezer. In some embodiments, the first arm and second arm are double-crossover tile arms. In some embodiments, a more ridged multi-helix origami assembly may be utilized. One embodiment of a DNA nano-tweezer in both the closed and open conformation is depicted in FIG. 1A. Conventional DNA nano-tweezer structures are known in the art. See for example Liu et al. ("A DNA tweezer-actuated enzyme nanoreactor," Nature Communications, 2013, 4:2127) and Zhou et al. ("Reversible regulation of protein binding affinity by a DNA machine," J. Am. Chem. Soc., 2012, 134(3), 1416-1418).

As used herein, "closed conformation" refers to the conformation of the DNA nano-tweezer wherein the hairpin loop is free and unbound by a trigger strand. In the closed conformation, the distance between the tip of the first arm and the tip of the second arm is about 4 nm (e.g., 3, 4, 5, or 6 nm). In some embodiments, the distance between the tip of the first arm and the tip of the second arm in the closed conformation is between about 3 nm and about 18 nm, between 3 nm and 16 nm, between 4 nm and 14 nm, or between 4 nm and about 10 nm. In some embodiments, the distance between the tip of the first arm and the tip of the second arm is less than 18 nm, less than 17 nm, less than 16 nm, less than 15 nm, less than 14 nm, less than 13 nm, less than 12 nm, less than 11 nm, less than 10 nm, less than 9 nm, less than 8 nm, less than 7 nm, less than 6 nm, less than 5 nm, less than 4 nm, less than 2 nm, or less than 1 nm.

As used herein, "open conformation" refers to the conformation of the DNA nano-tweezer wherein the trigger strand is bound to the hairpin loop. In the open conformation, the distance between the tip of the first arm and the tip of the second arm is about 16 nm (e.g., 12 nm, 13 nm, 14 nm, 15 nm, 16 nm, 17 nm, 18 nm, 19 nm, or 20 nm). In some embodiments, the distance between the tip of the first arm and the tip of the second arm in the open conformation is between about 12 nm and about 20 nm, between about 13 nm and about 19 nm, between about 14 nm and about 18 nm, or between about 15 nm and about 17 nm. In some embodiments, the distance between the tip of the first arm and the tip of the second arm in the open conformation is at least 12 nm, at least 13 nm, at least 14 nm, at least 15 nm, at least 16 nm, at least 17 nm, at least 18 nm, at least 17 nm, at least 20 nm, at least 30 nm, or at least 40 nm.

In various embodiments of the DNA nano-tweezers described herein, binding of the trigger loop to the hairpin loop results in an increase in the distance between the tip of the first arm and the tip of the second arm. The increase in distance may be an increase of about 8 nm, 10 nm, 11 nm, 12 nm, 13 nm, 14 nm, or 16 nm.

As used herein, "trigger strand" refers to a nucleic acid oligonucleotide that is complementary to and binds to the hairpin loop of the DNA nano-tweezer to initiate a conformation change in the DNA nano-tweezer from the closed conformation to the open conformation. The trigger strand may be between about 14 bases and about 40 bases (e.g., 15 to 35 bases, 18 to 30 bases, 20 bases to 28 bases) in length. In some embodiments, the trigger strand is about 21 bases in length (e.g., 15 bases, 16 bases, 17 bases, 18 bases, 19 bases, 20 bases, 21 bases, 22 bases, 23 bases, 24 bases, or 25 bases). In some embodiments, the trigger strand is a poly-T trigger strand that includes about 13 thymine (T) nucleotides, a poly-G trigger strand that includes about 13 guanine (G) nucleotides, or a poly-C trigger strand that includes about 13 cytosine (C) nucleotides. In some embodiments, one or more of the residues in the trigger strand are photocaged residues. In some embodiments, at least half of the residues in the trigger strand that are complementary to the hairpin loop are photocaged residues. In some embodiments, the trigger strand includes 5, 6, 7, 8, 9, 10, 11, 12 or 13 photocaged residues. In some embodiments, residues in the trigger loop alternate between regular nucleic acids and photocaged residues.

As used herein, "photocaged residues" refers to nucleic acids that have been modified with a photo-labile protecting group that is released from the nucleic acid upon exposure to a wavelength of light specific to the photo-labile protecting group. In some embodiments, the photo-labile protecting group is a nitrobenzyl caging group. In some embodiments the photocaged residues are modified with 6-nitropiperonyloxymethyl (NPOM) which is released from the residue upon exposure to UV light. In some embodiments, the photocaged resides are modified with a 1-(2-nitrophenyl)-1-ethyl (NPE) group which is released from the residue upon exposure to UV light. In some embodiments, the photocaged residues are modified with a 2-(2-nitrophenyl)ethyl (NPP) group which is released from the residue upon exposure to UV light. Synthesis and use of photocaged residues are known and understood in the art: see for example Buff et al. ("Light-activated nucleic acids 'caged' at the nucleobases," Chimia 63, 2009, 261-264), Walbert et al. ("Photolabile protecting groups for nucleosides: mechanistic studies of the 2-(2-nitrophenyl)ethyl group," Helvetica Chimica Acta, 2001, 84(6): 1601-1611), Pirrung et al. ("Photoremoveable protecting groups in DNA synthesis and microarray fabrication," Chapter 6 of Dynamic Studies in Biology: Phototriggers, Photoswitches and Caged Biomolecules, 2005), Dieters ("Light activation as a method of regulating and studying gene expression," Curr Opin Chem Biol, 2009, 13(5-6):678-686), and Lusic et al. ("A new photocaging group for aromatic N-herterocycles," Synthesis, 2006, 13:2147-2150), and Lusic et al. ("Photochemical DNA activation," Org. Lett., 2009, 9(10):1903-1906).

In some embodiments, the DNA nano-tweezers may additionally include a locking strand on each of the first and second arms to lock the DNA nano-tweezer in the closed conformation. The locking strands form a duplex that more tightly pulls the tips of the first and second arms closer together. The locking strands form a duplex of about 16 bp (e.g., 12 bp, 13 bp, 14 bp, 15 bp, 16 bp, 17 bp, 18 bp, 19 bp, or 20 bp). In some embodiments, the locking strand also includes a photocleavable backbone, which cleaves the backbone of the locking strand when exposed to UV light. In some embodiments, the locking strand includes an o-nitrobenzyl ester photocleavable backbone.

In some embodiments, the DNA nano-tweezers may additionally include a bound ligand, enzyme, active agent, antibody, cargo molecule, or other covalently or noncovalently linked moiety. In some embodiments, each arm of the DNA nano-tweezer is bound to a different ligand. In some embodiments, the DNA nano-tweezer is bound to ligands that bind dimeric receptors. In some embodiments, the first arm of the DNA nano-tweezer is bound to a ligand and the second arm is bound to a receptor for said ligand. In some embodiments, the DNA nano-tweezer is bound to one or more proteins. In some embodiments, the DNA nano-tweezer is bound to a polymer. In some embodiments, the DNA nano-tweezer is bound to a polymer and integrated into a larger material such as a hydrogel matrix.

In some embodiments, the DNA nano-tweezer may be labeled with a fluorescent label. In some embodiments, the DNA nano-tweezer may be labeled with two or more fluorescent labels. In some embodiments, the DNA nano-tweezer includes a donor-acceptor pair of fluorescent labels, such as would be useful for fluorescence resonance energy transfer (FRET) experiments.

In some embodiments, the DNA nano-tweezer is part of a nano-robot, nano-assembly, or nano-cage. Suitable DNA nano-cage assemblies have been previous described in that art. See for example U.S. Patent Publication No. 2018/0016569.

Also described herein are methods for reconfiguration of a DNA nano-tweezer described herein. Methods of reconfiguration of the DNA nano-tweezer include the step of exposing a DNA nano-tweezer described herein to a pulse of light for a length of time sufficient to release the protecting groups of the photocaged residues of the trigger loop, whereby the trigger loop binds to the single-stranded loop of the hairpin and the DNA nano-tweezer is reconfigured. In some embodiments, the pulse of light lasts between about 0.05 seconds and about 10 seconds, between about 1 second and about 9 seconds, between about 2 seconds and about 8 seconds or between about 1 second and about 6 seconds. In some embodiments, the light is UV light. In some embodiments, the light is UV light having a wavelength between about 300 nm and about 400 nm, between about 320 nm and about 390 nm, between about 330 nm and about 380 nm, or between about 350 nm and about 375 nm. In some embodiments, the light is UV light at a wavelength of about 365 nm.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates incorporation of a trigger strand into a DNA nanostructure from the outset while preventing it from binding to its target by modifying it with photocleavable protecting groups, thereby making it possible to actuate that structure with light. Light is an ideal stimulus for this purpose because it is clean, fast, and can be controlled in both space and time with high precision, especially for switching the target in the presence of cells. Furthermore, the high effective local concentration enforced by incorporating the trigger strand into the nanostructure should result in extremely fast kinetics, even at equimolar stoichiometry. Currently, the predominant mechanism for actuating DNA nanostructures using light employs the cis-trans isomerization of azobenzene-modified oligonucleotides to change the melting temperature of two complementary strands. Although this elegant approach is highly reversible, for many applications (for example, cargo release in a cell) a single switching is sufficient, or reversibility may be undesired. Furthermore, some azobenzenes can be reduced and inactivated by endogenous thiols inside of cells. Herein, we present the fast and irreversible switching between two states of a DNA nano-mechanical tweezer by incorporating a photocaged displacement strand into the structure and uncaging it with a brief pulse of ultraviolet (UV) light. Although a number of examples exist where toeholds are exposed through photo-cleavage reactions, [14] to our knowledge this is the first demonstration of direct photocaging of the displacement strand itself, providing a broadly applicable new mechanism for rapidly switching DNA nanostructures.

Our photoactivated nanostructure is based on a previously reported DNA tweezer design, which consists of two double-crossover tile arms linked by a crossover hinge (FIG. 1A). In this previous study, a single-stranded hairpin loop (red, 5'-TGCGTAAGACCCACAATCGCT-3', SEQ ID NO:9) serves as an actuation element between two arms. The nano-tweezer opening is driven by addition of an external DNA trigger strand (blue, 5'-CGTGTGGTTGAGCGATTGTGGGTCTTACGCA-3', SEQ ID NO:10) that is complementary to the loop. The opening kinetics and yield, however, depend on the trigger strand-to-tweezer molar ratio and diffusion in bulk.

Figure 1B:
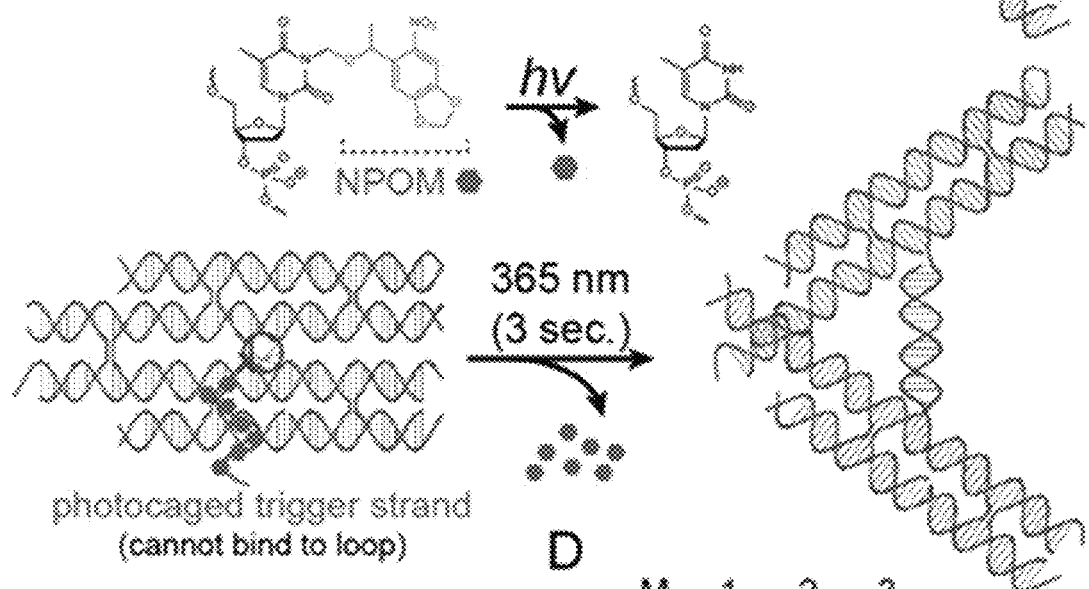

In the photo-tweezer design shown in FIG. 1B, the trigger strand (blue, 5'-TGCGXTXTXTXTXTXTXCGCT-3', SEQ ID NO:11) is incorporated into the structure by appending it to one of the component strands, and placed next to the regulatory hairpin loop (red, 5'-AGCGAAAAAAAAAAAAAACGCA-3', SEQ ID NO:12). Here, 7 thymidines (blue, X) in the internal trigger strand are protected with the 6-nitropiperonyloxymethyl (NPOM) caging groups pioneered by the Deiters group for regulating biological processes, thereby preventing hybridization between it and the hairpin loop. The photocaged strand was purchased from a commercial vendor, which will allow ready access to this technology. We reasoned that upon brief exposure to UV light, the NPOM groups would be rapidly cleaved, allowing the internal trigger strand to hybridize with the loop and open the tweezer.

Figure 1C:
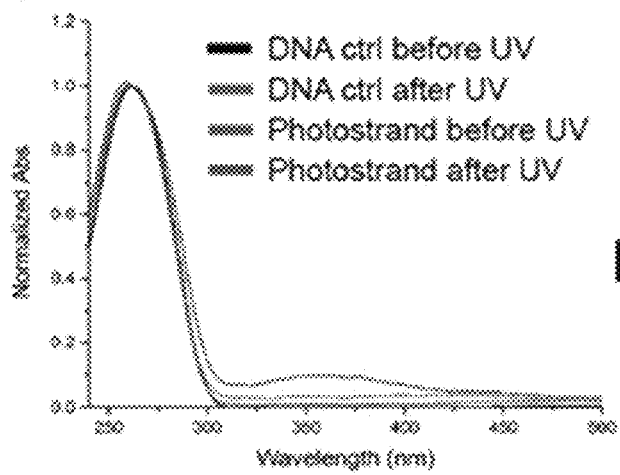
Figure 1D:
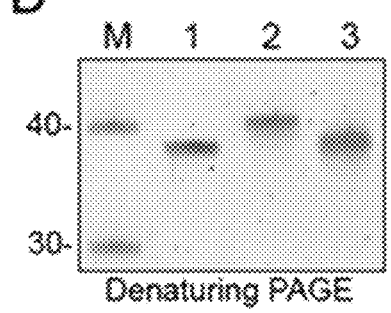
Figure 1E:
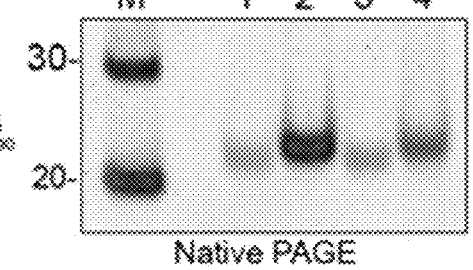

We first monitored the deprotection process by UV/Vis spectroscopy (FIG. 1C). The NPOM group has a signature absorbance at 365 nm, which was readily observed for the photocaged trigger strand containing 7 cages (blue). However, after UV illumination for 3 s the peak was reduced almost to baseline due to removal of cages (purple). We estimate that more than 85% of cages were removed by this brief pulse as determined from the UV/Vis spectrum. Control DNA oligonucleotides with the same sequence did not show the 365 nm peak before or after UV irradiation. The deprotection of cage groups was further observed by denaturing polyacrylamide gel electrophoresis (PAGE) (FIG. 1D). The band corresponding to the caged strand (lane 2) quantitatively shifted to a faster migrating band (lane 3) with the same mobility as the non-protected control strand (lane 1). By native PAGE (FIG. 1E), the photocaged strand (lane 3) did not bind to its complementary polyA strand until after deprotection by UV (lane 4), and the duplex has the same mobility as a control strand-polyA duplex in lane 2.

Figures 2A, 2B, 2C:
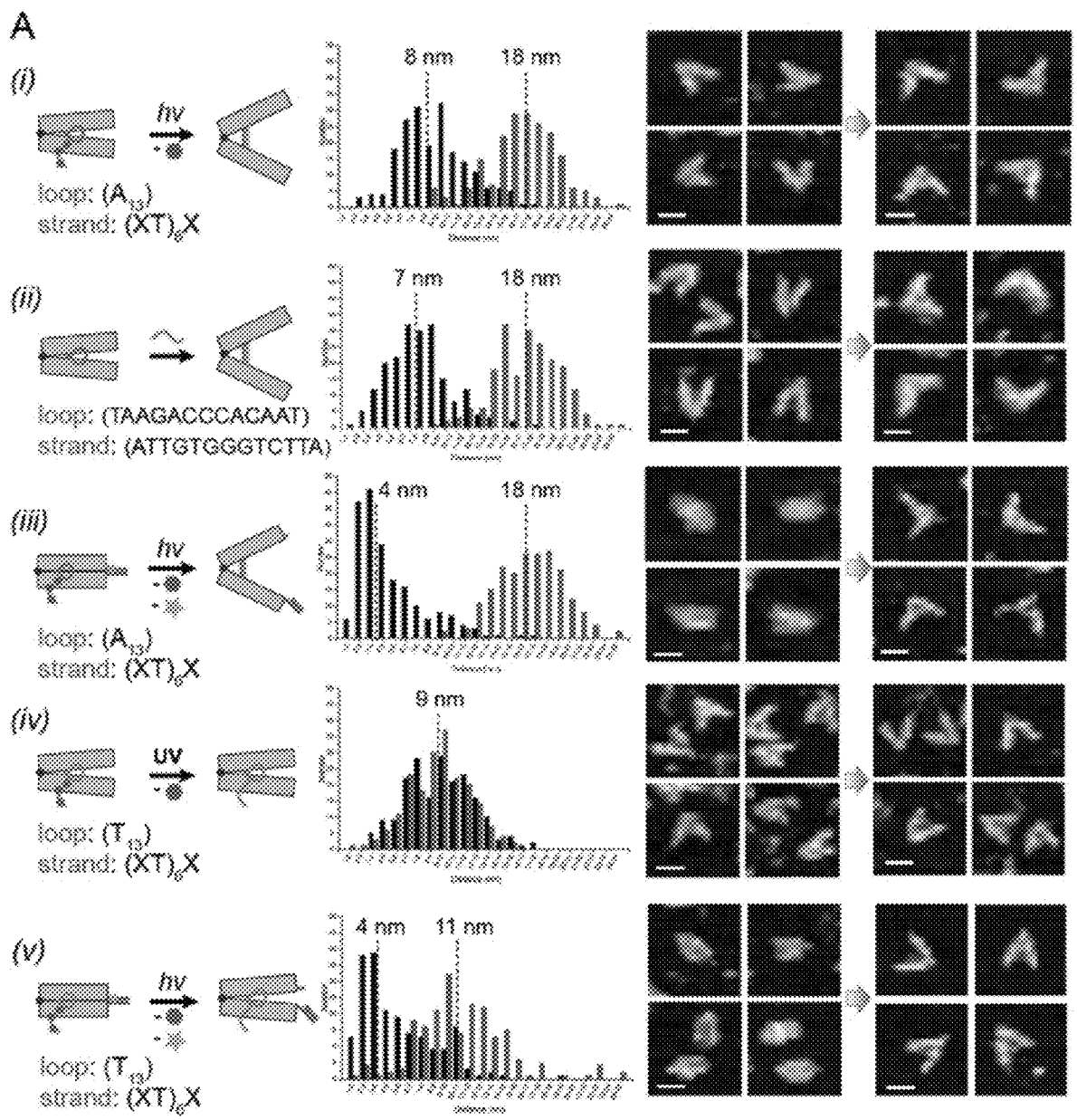
FIGS. 2A-2C show characterization of dynamic tweezer actuation with light. A) Distance histograms between the ends of the tweezer arms, based on AFM imaging. Systems: i) photocaged tweezer, ii) original tweezer actuated by an external trigger strand, iii) photocaged tweezer with photocleavable locking strands, iv) negative control for photocaged tweezer without locking strands, v) negative control for photocaged tweezer with locking strands. Scale bars: 15 nm. B) Detailed design of photocaged tweezer System (iii) with locking strands. C) FRET efficiency measurements for Systems (i)-(v). Error bars indicate the standard deviation for n=3 independent measurements. Sequences included in FIGS. 2A-2C include $A_{13}$ (SEQ ID NO: 1), $(XT)_6X$ (wherein X is a photocaged thymidine residue, SEQ ID NO:2), TAAGACCCACAAT (SEQ ID NO:3), ATTGTGGGTCTTA (SEQ ID NO:4), and $T_{13}$ (SEQ ID NO:5).
Figure 7:
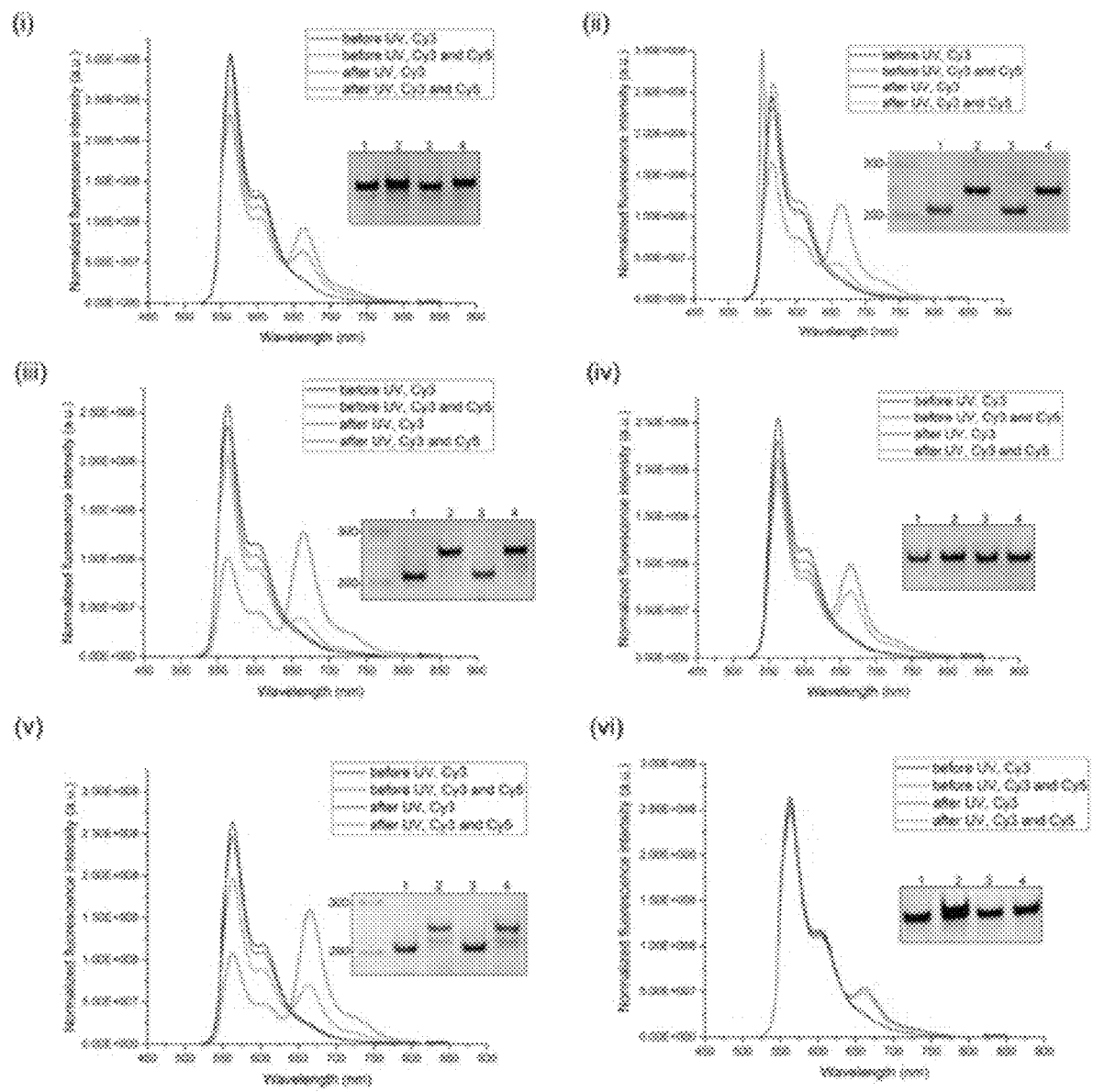
FIG. 7 shows FRET measurements of nano-tweezer samples Systems (i) to (ix). (i) photocaged tweezer, unlocked; (ii) original tweezer actuated by an external trigger strand; (iii) photocaged tweezer with locking strands; (iv) analogue of System (i) with $polyT_{13}$ loop and photocaged internal strand; (v) analogue of System (iii); (vi) control tweezer with polyA loop and internal polyT strand; (vii) locked tweezer with polyA loop and internal polyT strand; (viii) control tweezer with only internal photocaged strands; (ix) locked tweezer with only internal photocaged strand. Lane 1 and black curve: tweezers with Cy3 only before UV exposure; lane 2 and blue curve: tweezers with Cy3 only after UV exposure; lane 3 and red curve, tweezers with Cy3-Cy5 before UV exposure; lane 4 and purple curve: tweezers with Cy3-Cy5 after UV exposure.
Figure 7:
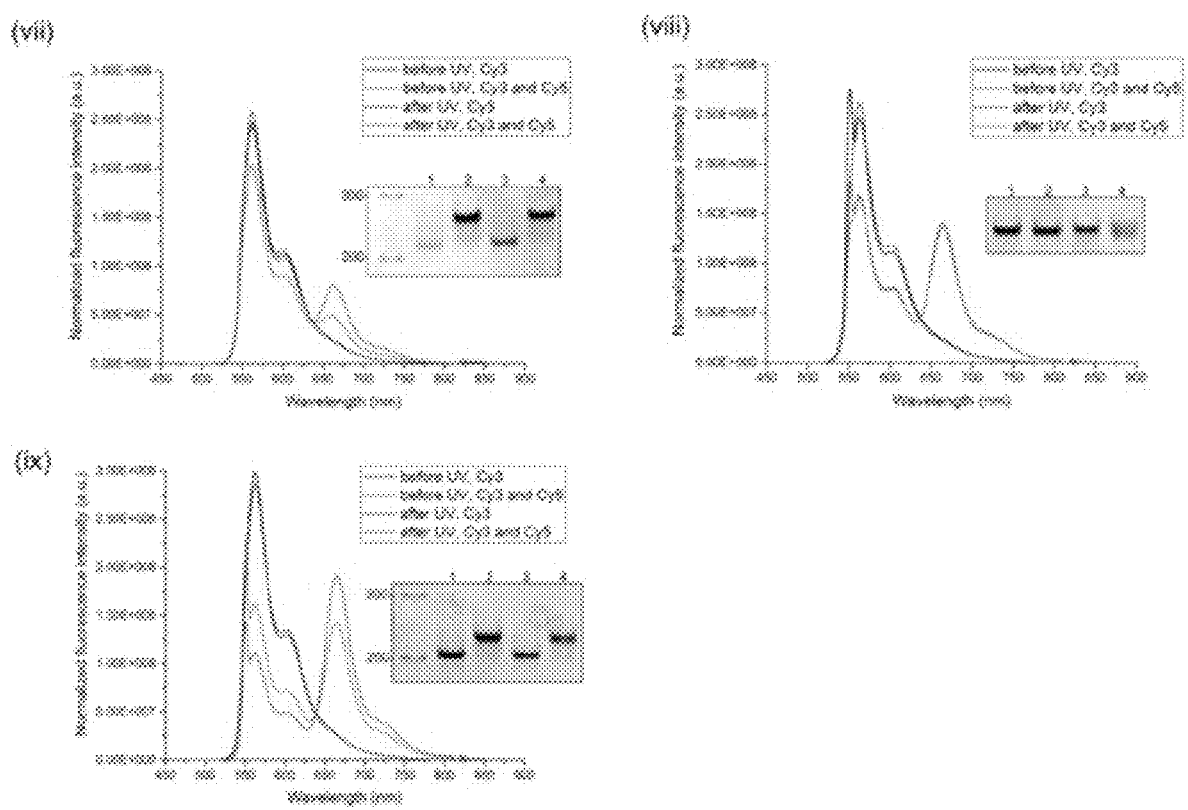
Figures 8A, 8B, 8C, 8D:
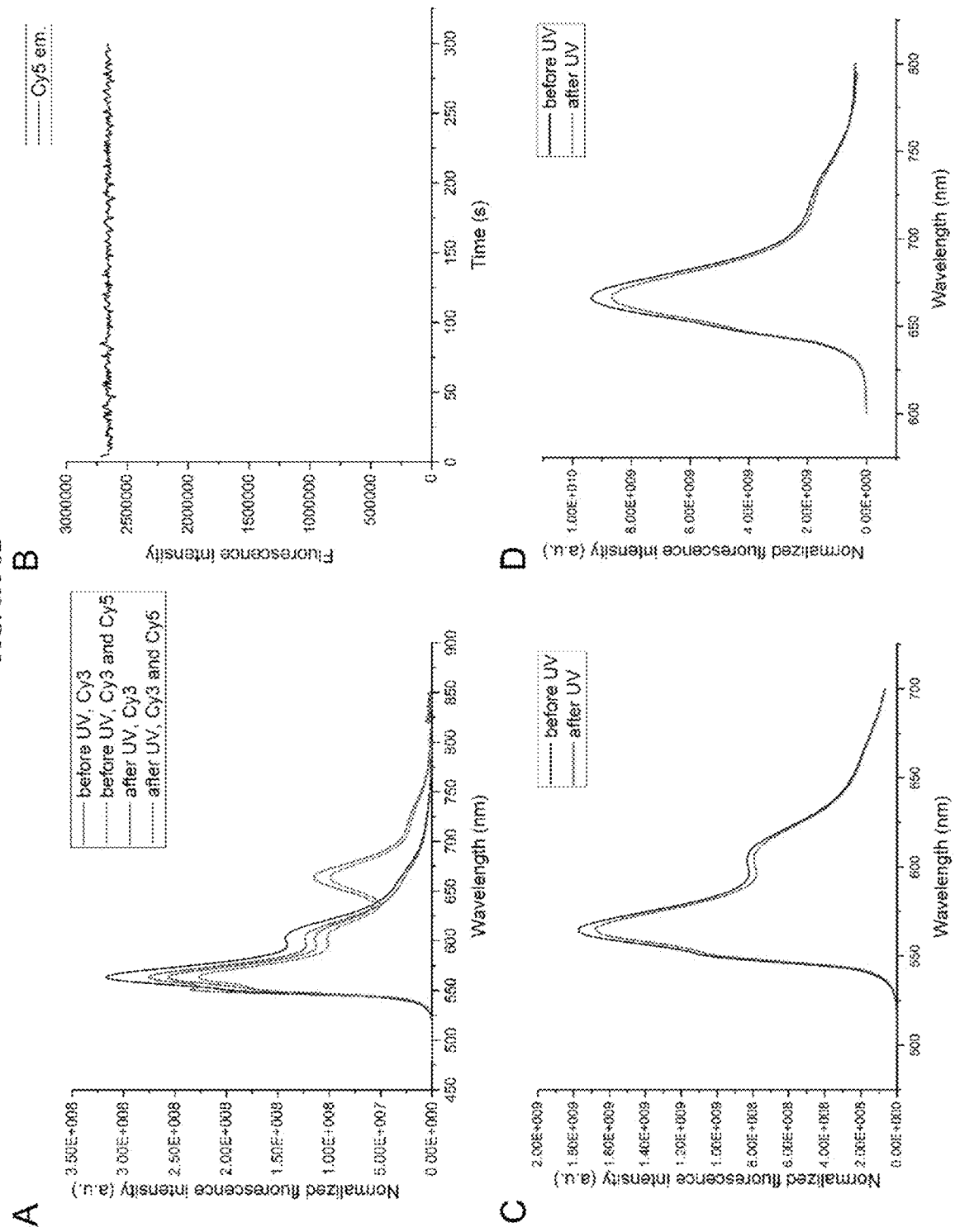
FIG. 8A-8D show FRET measurement of a nano-tweezer (FIG. 1B) and emission spectra of Cy3/Cy5 labeled DNA. A) Bulk FRET measurement of nano-tweezer in FIG. 1B. B) Real-time Cy5 emission of nano-tweezer in FIG. 1B. C) Emission spectra of Cy3 labeled DNA oligo before and after UV exposure. D) Emission spectra of Cy5 labeled DNA oligo before and after UV exposure to confirm that the fluorophores were not significantly damaged by the UV illumination.
Figure 9:
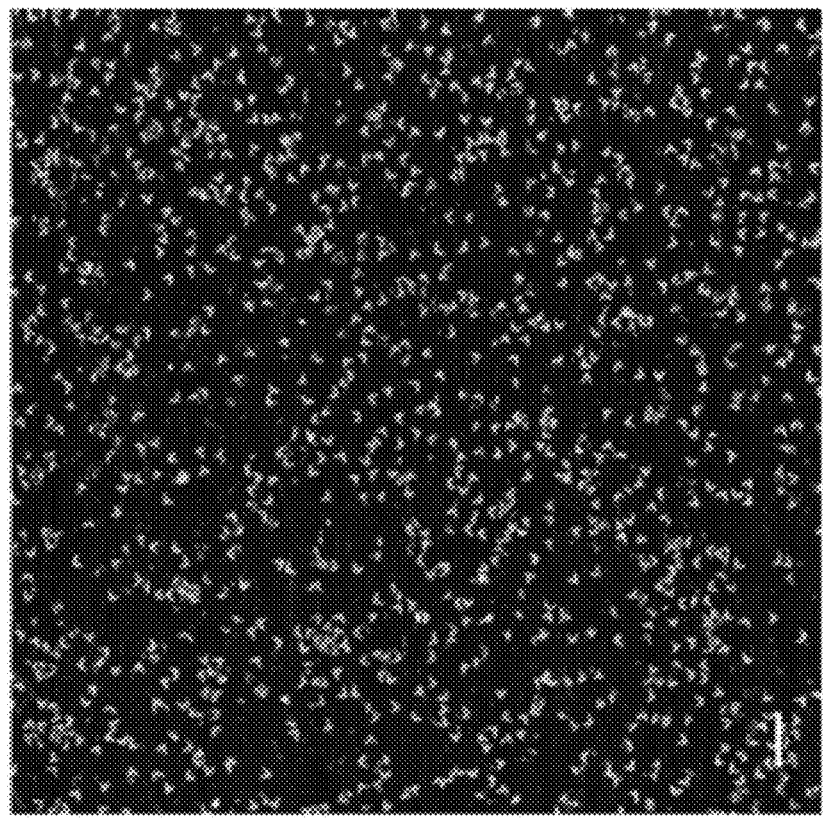
FIG. 9 shows Zoom-out AFM images of System i. Scale bar: 100 nm.
Figure 9:
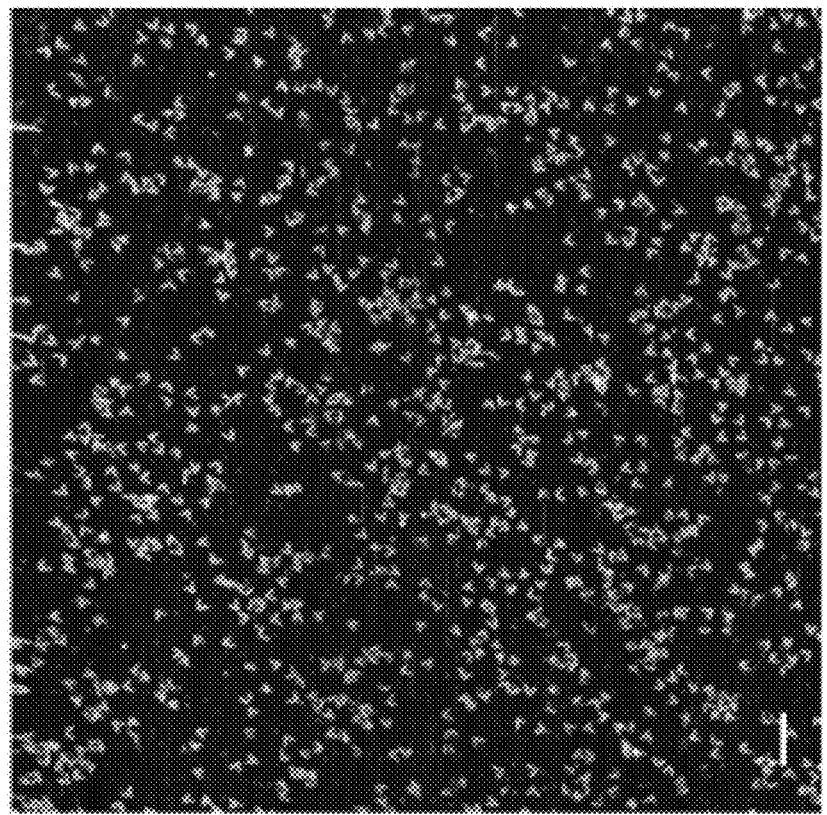
Figure 10:
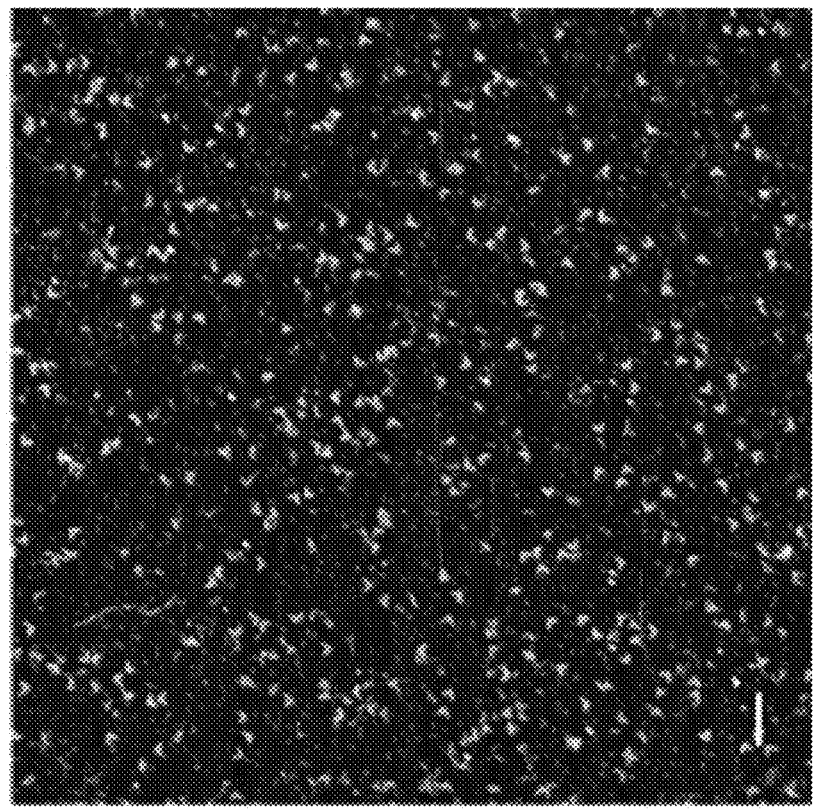
FIG. 10 shows Zoom-out AFM images of System ii. Scale bar: 100 nm.
Figure 10:
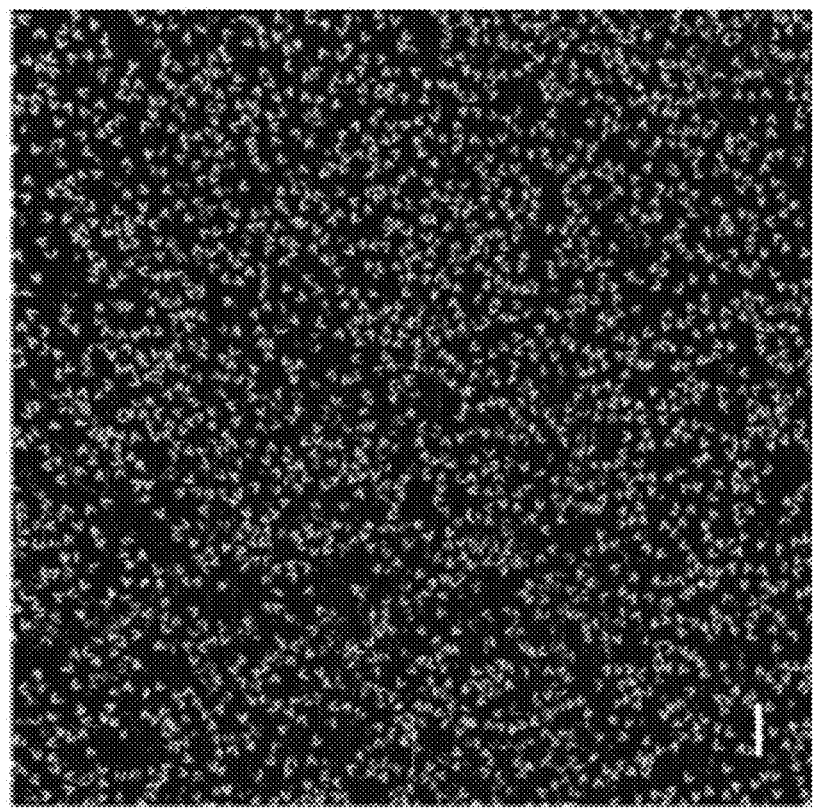
Figure 11:
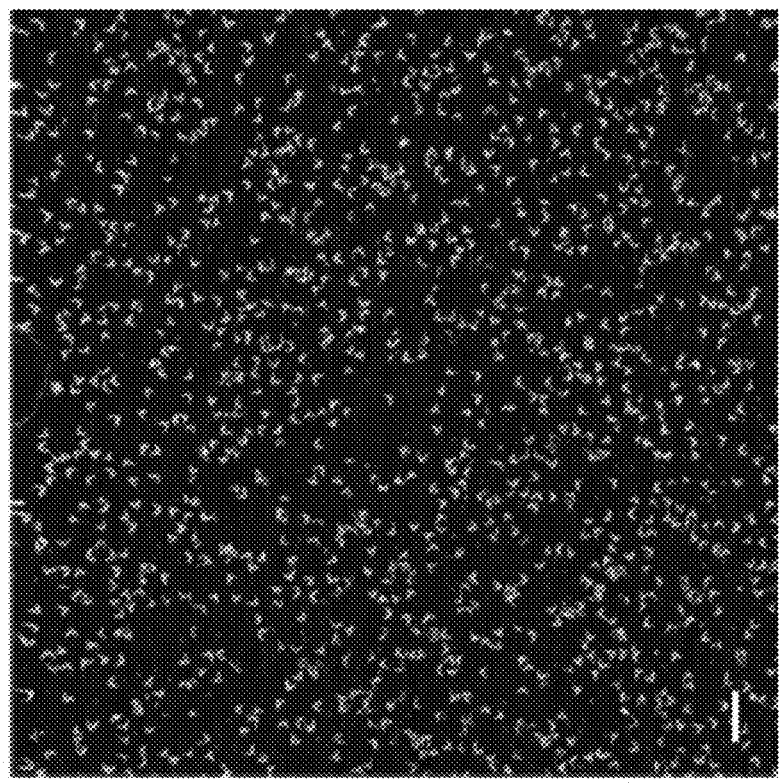
FIG. 11 shows Zoom-out AFM images of System iii. Scale bar: 100 nm.
Figure 11:
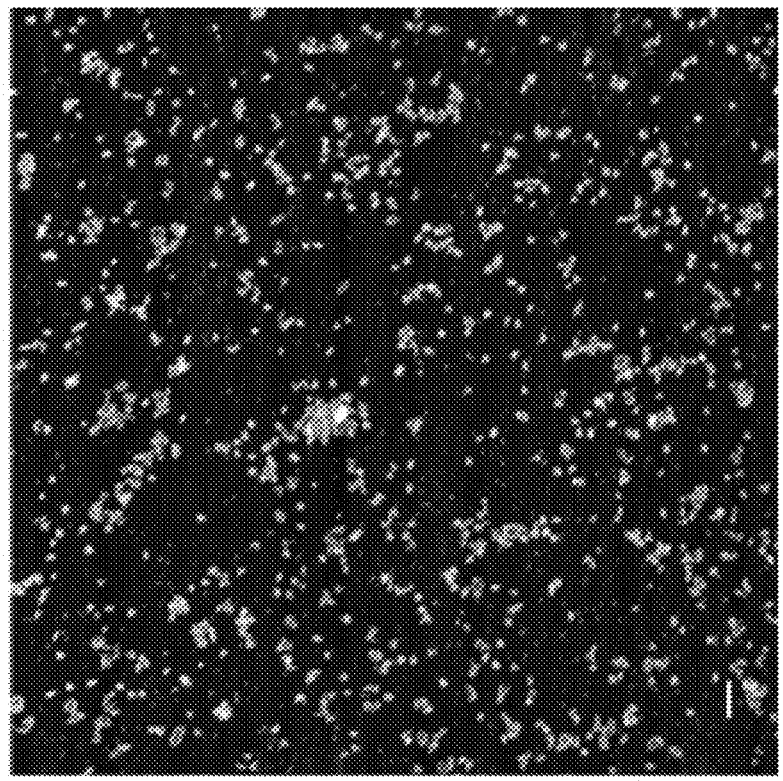
Figure 12:
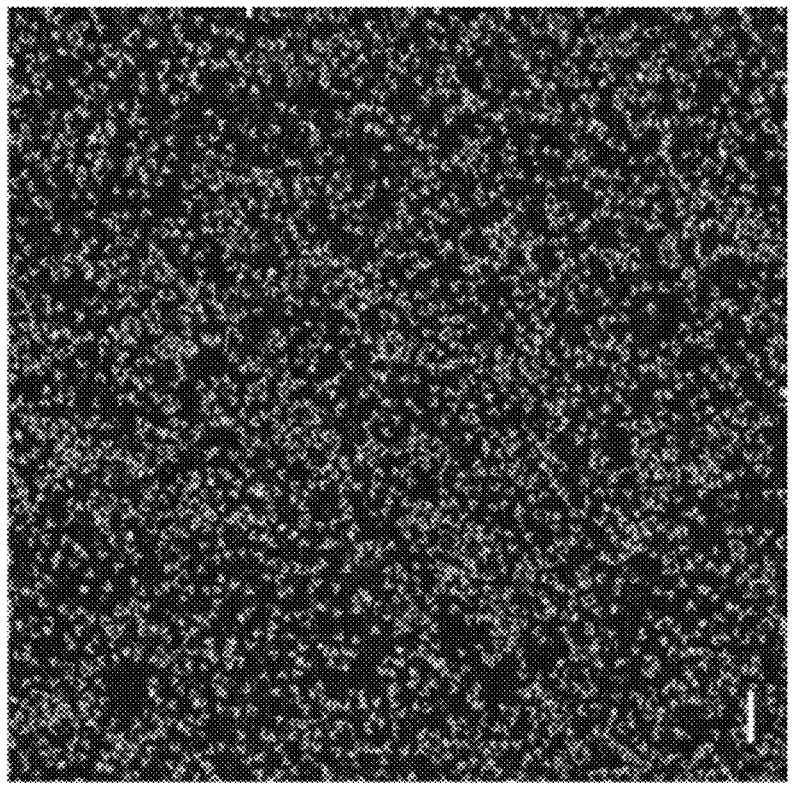
FIG. 12 shows Zoom-out AFM images of System iv. Scale bar: 100 nm.
Figure 12:
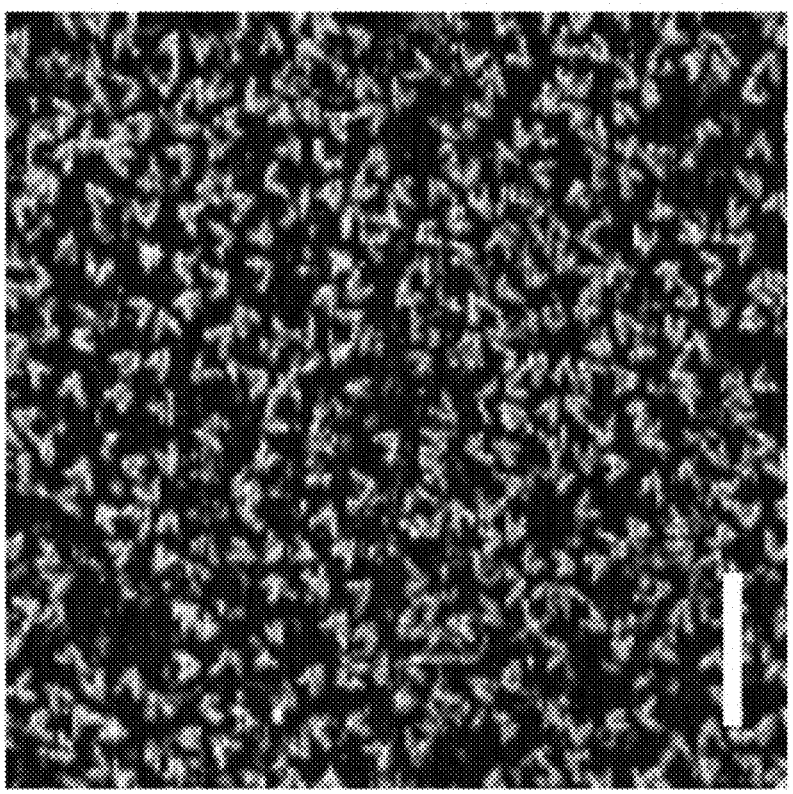
Figure 13:
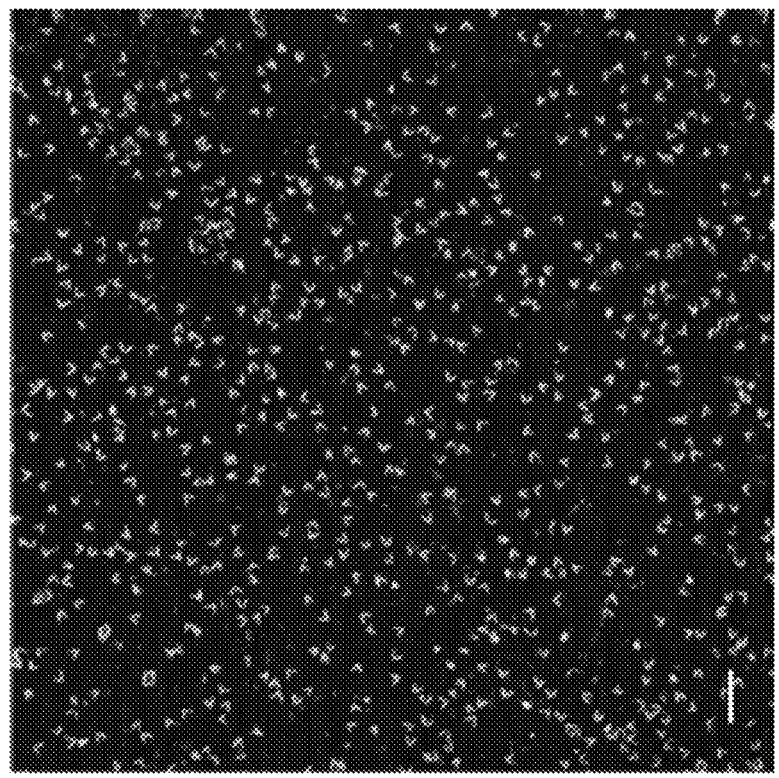
FIG. 13 shows Zoom-out AFM images of System v. Scale bar: 100 nm.
Figure 13:
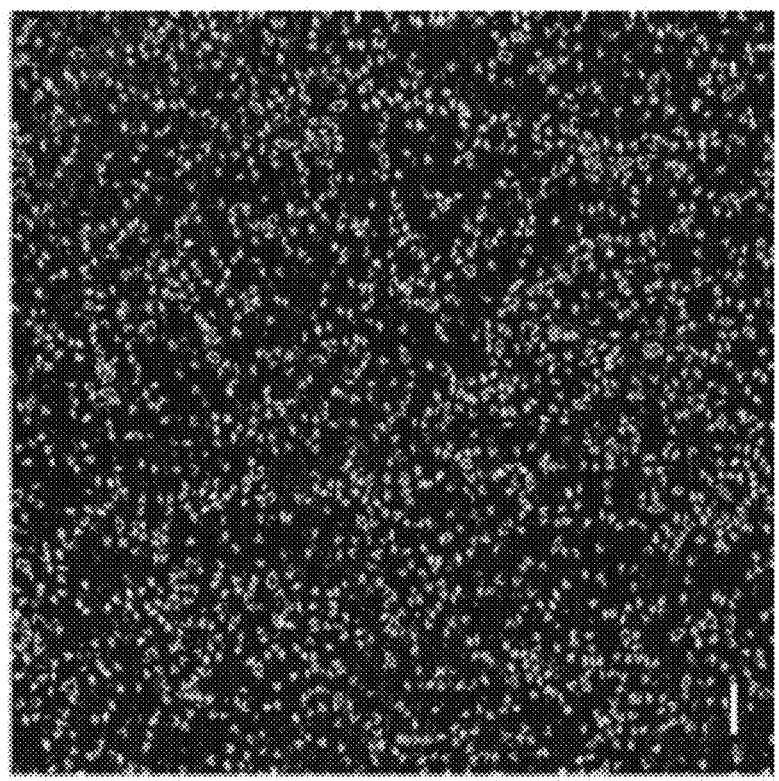

Next, we assembled tweezers bearing both the hairpin loop and the photocaged displacement strand, and probed the UV light-induced opening by both atomic force microscopy (AFM) and Förster resonance energy transfer (FRET) with a Cy3-Cy5 donor-acceptor pair (System (i), FIGS. 2A, 2C). Before irradiation, the tweezers displayed a distribution of distances between the ends of the inner arms (measured by AFM) centered around 8 nm. Following UV illumination, however, the tweezers shifted to a more open population centered around 18 nm, closely matching the predicted model. In several images, the duplex holding the arms apart can be clearly visualized, further supporting our proposed mechanism. We note that the broad distributions of both the closed and open states are expected due to the relative flexibility of the tweezer; more rigid multi-helix origami assemblies could be used in the future to narrow the distance distribution. The opening was further supported by FRET (FIG. 7), with a drop from 22.9% to 15.0% efficiency from the closed to the open state, which we confirmed was not due to damage of the dyes to the UV illumination (FIGS. 8C-8D). We were unable to correlate the FRET efficiency with precise distances, however, owing to the restricted rotation of the internally placed donor-acceptor dye pair, which precludes the usual approximation of $k2=\frac{2}{3}$ in the Förster equation for freely rotating dyes. As a result, FRET could only be used to qualitatively validate the AFM histograms.

We next compared System (i) with the original tweezer actuated by an external trigger strand (System (ii)). By both AFM and FRET, we observed a similar shift from the closed to the open states as for the photo-tweezer. The closed state distance distribution for System (ii) was centered around a slightly smaller distance by both measurements, which we attribute to the polyA hairpin loop in System (i) forcing the tweezer slightly more open due to enhanced base-stacking of the adenine residues. Interestingly, when we attempted to open a polyA hairpin tweezer with an externally added polyT trigger strand, no appreciable opening was observed (FIG. 4B, FIGS. 8A-8D), which is most likely due to the weaker A-T interactions in this system compared with the optimized sequence containing several C-G pairs in System (ii). This result highlights the potent effect of high local concentration in the photo-tweezer driving interactions that would not be possible in the bulk solution.

Although the photo-tweezer behaved quite similarly to the original, externally actuated system, the overlapping distance distributions and the switch from 8 to 18 nm may not be sufficient for some applications. Both Systems (i) and (ii) are partly open even in the closed state (8 nm vs. ca. 4 nm expected from the model), which is most likely due to electrostatic repulsion between the arms, the flexibility of a tweezer held together by a single crossover at the hinge, and the presence of only 3 base pairs in the stem of the hairpin loop. We thus next asked if we could assemble a more compact closed state by extending the two arms with two complementary locking strands that could form a 16-bp duplex (System (iii), FIG. 2B). To render the system photoresponsive, we introduced an o-nitrobenzyl ester photocleavable backbone modification (orange star), which has a maximum absorbance between 300 and 350 nm, into one of the locking strands. We reasoned that upon UV illumination, the backbone cleavage would release the locker strands simultaneously with NPOM cleavage, allowing the tweezer to switch to the open state. Indeed, prior to UV exposure System (iii) showed a peak inter-arm distance around 3-4 nm, but the open tweezer distribution was virtually identical to System (i) at 18 nm. Relative to System (i), the FRET efficiency for System (iii) was significantly enhanced for the closed state (58.2%), and slightly lower for the open state (10.3%). Furthermore, there is virtually no overlap in the distance histograms between the closed and open states for System (iii), which will be useful especially for applying forces on biological systems like proteins that require a clear differentiation of the two states.

As controls, we generated analogues of Systems (i) and (iii), termed Systems (iv) and (v), respectively, but with a polyT hairpin loop that should not bind to the internal trigger strand after removing the photocages. As expected, both of these controls were similar to their respective systems in the closed configurations by both AFM and FRET. However, after irradiation, System (iv) showed no change in the distance distribution, confirming the inability of the trigger strand to bind the hairpin. System (v) showed a broad open configuration after UV irradiation, which was perhaps due to additional electrostatic repulsion introduced by the duplex locker strands, yet was clearly less open than System (iii).

Figure 3A:
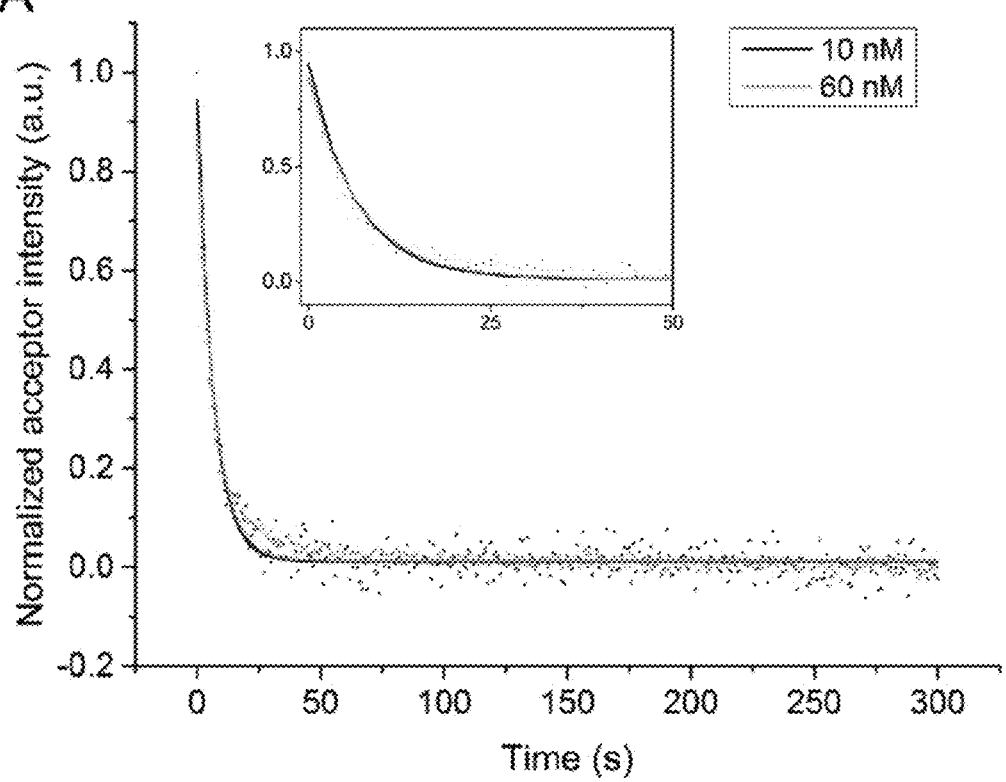
FIGS. 3A-3B show normalized kinetic curves of the tweezer opening. A) Time-dependent FRET of the photo-actuated tweezer at 10 nm and 60 nm; no concentration dependence was observed. The rate constant was acquired by fitting the kinetic curve to an integrated first order reaction equation. B) Time-dependent FRET of the externally actuated tweezer at 60 nm, with varying concentrations of the trigger strand. The rate constant was acquired by fitting the kinetic curve to an integrated second order reaction equation. Insets: zoom-in plot of the first 50 s of the corresponding kinetic curves.
Figure 3B:
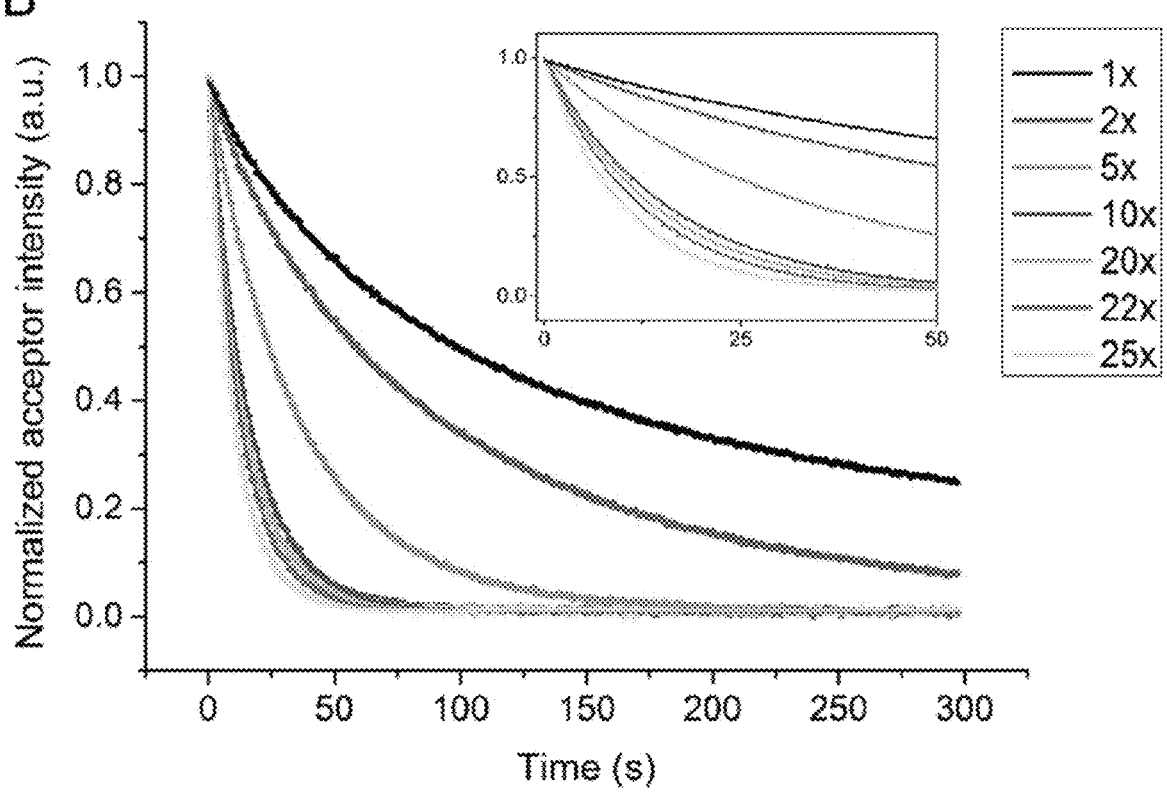
Figures 4A, 4B, 4C, 4D:
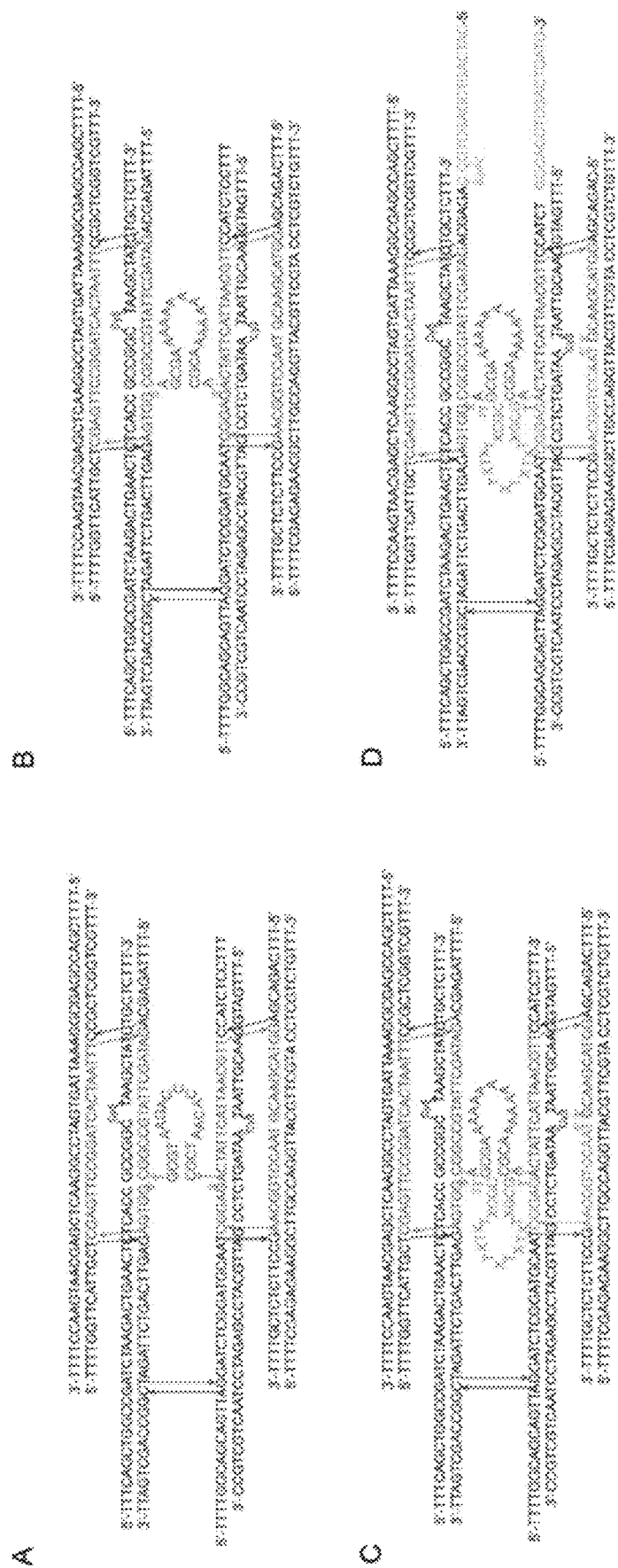
FIGS. 4A-4D show DNA sequence design for original DNA nano-tweezers with random loop sequence, polyA loop sequence and photocaged DNA nano-tweezers. A) The original DNA nano-tweezers with random loop sequence (SEQ ID NOs:13, 15, 17, 18, 19, 20, 21, 22, and 23, FIG. 2(ii)). Opening of hairpin depends on addition of external trigger strand, which is complementary to the hairpin. B) The original DNA nano-tweezers with polyA loop sequence (SEQ ID NOs:13, 15, 17, 18, 19, 20, 22, 23, and 34, FIGS. 8A-8B). C) Photocaged DNA nano-tweezers without locking strands (SEQ ID NOs:13, 15, 17, 18, 19, 20, 22, 23, 24, and 25, FIG. 2(i)). D) Photocaged DNA nano-tweezers with locking strands (SEQ ID NOs: 13, 15, 17, 18, 19, 20, 24, 25, 26, and 27, FIG. 2(iii)).

Having demonstrated that the photocaged displacement strand approach was efficient and stimulus-responsive, we next turned to characterizing the kinetics of the system. A central hypothesis of our approach is that the high local concentration of the photocaged strand should allow for much more rapid nanostructure actuation compared with externally added strands. To probe this effect, we carried out a series of time-dependent FRET experiments (monitoring Cy5 acceptor emission), triggering tweezer opening with either UV light or increasing concentrations of the external trigger strand, with Systems (iii) and (ii), respectively (FIGS. 3A-3B). For System (iii), UV irradiation resulted in a rapid drop in Cy5 emission, reaching a minimum value after only 25 seconds (FIG. 3A). The normalized kinetic traces were independent of tweezer concentration (10 vs. 60 nm), as expected for this effectively unimolecular process. To quantify the opening, we fitted the curves to equations (1) and (2), and calculated the time to reach 90% of the open FRET emission, defined as t90 (Table 1). For System (iii), t90=15 s. By contrast, 1 equivalent of externally added trigger strand for System (ii) (at a tweezer concentration of 60 nm) showed dramatically slower kinetics (FIG. 3B), with t90=915 s, corresponding to a roughly 60-fold rate reduction relative to the internally incorporated photocaged strand. Even at 25 equivalents of trigger strand (1.5 mm concentration) t90=24 s, which was still slower than System (iii).

Taken together, our results highlight the great potential for internal photocaged displacement strands as a way to switch quickly and irreversibly between two conformational states for a nano-mechanical device. We envision that this approach will be particularly useful for exerting forces on biological systems at the nanoscale in a highly stimulus-responsive manner. For example, functionalizing the tweezers with ligands that bind dimeric receptors would allow one to rapidly break the protein interaction with light and probe biological effects. Toward this end, we used computational simulations to estimate the range of forces that can be applied by System (iii) as up to about 46 pN, which is well within the range of many biological sensing events. The above experiments used a brief, intense UV pulse that proved harmful to cells (ca. 50% survival). However, by reducing the exposure time and using a UV source with an emission spectrum more narrowly tailored to the NPOM absorbance, we were able to improve cell survival to >85%, making our system relevant for biological studies with live cells. Finally, we note that by designing multiple displacement strands, with orthogonal sequences, it should be possible to reconfigure complex DNA nanostructures (for example, 3D origami assemblies), leading to light-activated nano-robots, spring-loaded mechanical assemblies, or on-demand cargo release from a targeted nano-cage.

Materials

DNA Strands:

Single-stranded oligonucleotides, fluorophore (Cy3/Cy5)-modified oligonucleotides and photo-cleavable linker modified oligonucleotides were purchased from IDT DNA (Integrated DNA Technologies, Inc.). Photocaged oligonucleotides were purchased from Bio-Synthesis, Inc. (Lewisville, Tex.).

Buffers:

Tris base, acetic acid, EDTA, and magnesium acetate were purchased from Sigma Aldrich.

Cell Lines:

KB (ATCC® CCL-17™), 293 [HEK-293] (ATCC® CRL-1573™) and Hep G2 [HEPG2] (ATCC® HB-8065™) were purchased from ATCC.

Cell Culture Media and Cell Viability Assay Reagents:

Dulbecco's Modification of Eagle's Medium (DMEM) was purchased from Corning. Supplemental Fetal Bovine Serum (FBS) was purchased from Atlanta Biologicals, Inc. Penicillin, Steptomycin and Amphotericin B antibiotics were purchased from Lonza.

Design, Assembly, and Characterization of DNA Nano-Tweezers

DNA nanostructure design: The detailed sequence designs of the original DNA Nano-tweezers and photocaged DNA nano-tweezers are shown in FIGS. 4A-4D. Tiamat (downloaded from yanlab.asu.edu/Resources.html) was used for structure and sequence design. All sequences are written in 5'-3' order.

```
Sequences of original DNA nano-tweezers:
T1:
                                    (SEQ ID NO: 13)
TTTTCGACCGAGCGGAAATTAGTGATCCGGAACTCGAGCAATGAACCTT TT
T2:
                                    (SEQ ID NO: 14)
TTTCAGCTGGCCGATCTAAGACTGAACTCTCACCGCCGGCATAAGCTAT

CTGCTCTTT

T2-iCy5:
                                    (SEQ ID NO: 15)
TTTCAGCTGGCCGATCTAAGACTGAACTCTCACCGCCGGC/iCy5/TAA

GCTATCTGCTCTTT

T3:
                                    (SEQ ID NO: 16)
TTTGATGGAACGTTAATGAATAGTCTCCGATTGCATCCGAGATCCTAAC

TGCTGCC

T3-iCy3:
                                    (SEQ ID NO: 17)
TTTGATGGAACGTTAAT/iCy3/AATAGTCTCCGATTGCATCCGAGATC

CTAACTGCTGCC

T4:
                                    (SEQ ID NO: 18)
TTTTCGAGAGAAGGCTTGCCAGGTTACGTTCGTACCTCGTCTGTTT

T5:
                                    (SEQ ID NO: 19)
TTTTGGCAGCAGTTACGGCCAGCTGATT

T6:
                                    (SEQ ID NO: 20)
TTTTGGTTCATTGCTGAGTTCAGTCTTAGATGGATCTCGGATGCAATGC

CTTCTCTCGTTTT
```

-continued

T7:
(SEQ ID NO: 21)
GGTGACGAGTTCCGGATCACTAATTTGATAGCTTATGCCGGCTGCGTAA

GACCCACAATCGCTACTATTCATTAACGTTGGTACGAACGTAACCTGGC

AACGGAG

T8:
(SEQ ID NO: 22)
TTTTAGAGCACCGCTCGGTCGTTT

T9:
(SEQ ID NO: 23)
TTTCAGACGACCATCTCCTTT

External trigger strand:
(SEQ ID NO: 10)
CGTGTGGTTGAGCGATTGTGGGTCTTACGCA

Sequences of photocaged DNA nano-tweezers without locking strands
T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-Aloop:
(SEQ ID NO: 24)
GGTGACGAGTTCCGGATCACTAATTTGATAGCTTATGCCGGCAGCGAAA

AAAAAAAAAACGCAACTATTCATTAACGTTGGTACGAACG

T7-2-photocage:
(SEQ ID NO: 25)
TAACCTGGCAACGGAGTGCGXTXTXTXTXTXTXCGCT

T8:
(SEQ ID NO: 22)
TTTTAGAGCACCGCTCGGTCGTTT

T9:
(SEQ ID NO: 23)
TTTCAGACGACCATCTCCTTT

Sequences of photocaged DNA nano-tweezers with locking strands
T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-Aloop:
(SEQ ID NO: 24)
GGTGACGAGTTCCGGATCACTAATTTGATAGCTTATGCCGGCAGCGAAA

AAAAAAAAAACGCAACTATTCATTAACGTTGGTACGAACG

T7-2-photocage:
(SEQ ID NO: 25)
TAACCTGGCAACGGAGTGCGXTXTXTXTXTXTXCGCT

T8-lock-PC:
(SEQ ID NO: 26)
CATCAGTCGAGCTGC/iSpPC/CAGAGCACCGCTCGGTCGTTT

T9-lock:
(SEQ ID NO: 27)
CAGACGACCATCTGGCAGCTCGACTGATG

Sequences of control group (polyA loop and internal polyA strand) without locking strands
T1:
(SEQ ID NO: 13)
TTTTCGACCGAGCGGAAATTAGTGATCCGGAACTCGAGCAATGAACCTT

TT

-continued

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-Aloop:
(SEQ ID NO: 24)
GGTGACGAGTTCCGGATCACTAATTTGATAGCTTATGCCGGCAGCGAAA

AAAAAAAAAACGCAACTATTCATTAACGTTGGTACGAACG

T7-2-polyA:
(SEQ ID NO: 28)
TAACCTGGCAACGGAGTGCGAAAAAAAAAAAAAACGCT

T8:
(SEQ ID NO: 22)
TTTTAGAGCACCGCTCGGTCGTTT

T9:
(SEQ ID NO: 23)
TTTCAGACGACCATCTCCTTT

Sequences of control group (polyA loop and internal polyA strand) with locking strands
T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-Aloop:
(SEQ ID NO: 24)
GGTGACGAGTTCCGGATCACTAATTTGATAGCTTATGCCGGCAGCGAAA

AAAAAAAAAACGCAACTATTCATTAACGTTGGTACGAACG

T7-2-polyA:
(SEQ ID NO: 28)
TAACCTGGCAACGGAGTGCGAAAAAAAAAAAAAACGCT

T8-lock-PC:
(SEQ ID NO: 26)
CATCAGTCGAGCTGC/iSpPC/CAGAGCACCGCTCGGTCGTTT

T9-lock:
(SEQ ID NO: 27)
CAGACGACCATCTGGCAGCTCGACTGATG

Sequences of control group (only internal photocaged strand) without locking strands
T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

-continued

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-no loop:
(SEQ ID NO: 29)
GGTGACGAGTTCCGGATCACTAATTTGATAGCTTATGCCGGCAGCGCGC

AACTATTCATTAACGTTGGTACGAACG

T7-2-photocage:
(SEQ ID NO: 25)
TAACCTGGCAACGGAGTGCGXTXTXTXTXTXTXCGCT

T8:
(SEQ ID NO: 22)
TTTTAGAGCACCGCTCGGTCGTTT

T9:
(SEQ ID NO: 23)
TTTCAGACGACCATCTCCTTT

Sequences of control group (only internal photocaged strand) with locking strands

T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-1-no loop:
(SEQ ID NO: 29)
GGTGACGAGTTCCGGATCACTAATTTGATAGCTTATGCCGGCAGCGCGC

AACTATTCATTAACGTTGGTACGAACG

T7-2-photocage:
(SEQ ID NO: 25)
TAACCTGGCAACGGAGTGCGXTXTXTXTXTXTXCGCT

T8-lock-PC:
(SEQ ID NO: 26)
CATCAGTCGAGCTGC/iSpPC/CAGAGCACCGCTCGGTCGTTT

T9-lock:
(SEQ ID NO: 27)
CAGACGACCATCTGGCAGCTCGACTGATG

Sequences of control group (polyT loop and internal photocaged strand) with locking strands

T1:
(SEQ ID NO: 13)
TTTTCGACCGAGCGGAAATTAGTGATCCGGAACTCGAGCAATGAACCTT

TT

T2:
(SEQ ID NO: 14)
TTTCAGCTGGCCGATCTAAGACTGAACTCTCACCGCCGGCATAAGCTAT

CTGCTCTTT

T2-iCy5:
(SEQ ID NO: 15)
TTTCAGCTGGCCGATCTAAGACTGAACTCTCACCGCCGGC/iCy5/TAA

GCTATCTGCTCTTT

T3:
(SEQ ID NO: 16)
TTTGATGGAACGTTAATGAATAGTCTCCGATTGCATCCGAGATCCTAAC

TGCTGCC

T3-iCy3:
(SEQ ID NO: 17)
TTTGATGGAACGTTAAT/iCy3/AATAGTCTCCGATTGCATCCGAGATC

CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC

CTTCTCTCGTTTT

T7-Tloop:
(SEQ ID NO: 30)
GGTGACGAGTTCCGGATCACTAATTTGATAGCTTATGCCGGCAGCGTTT

TTTTTTTTCGCAACTATTCATTAACGTTGGTACGAACG

T7-2-photocage:
(SEQ ID NO: 25)
TAACCTGGCAACGGAGTGCGXTXTXTXTXTXTXCGCT

T8-lock-PC:
(SEQ ID NO: 26)
ATCAGTCGAGCTGC/iSpPC/CAGAGCACCGCTCGGTCGTTT

T9-lock:
(SEQ ID NO: 27)
CAGACGACCATCTGGCAGCTCGACTGATG

Sequences of control group (polyT loop and
internal photocaged strand) without locking
strands

T1:
(SEQ ID NO: 13)
TTTTCGACCGAGCGGAAATTAGTGATCCGGAACTCGAGCAATGAACCTT
TT

T2:
(SEQ ID NO: 14)
TTTCAGCTGGCCGATCTAAGACTGAACTCTCACCGCCGGCATAAGCTAT
CTGCTCTTT

T2-iCy5:
(SEQ ID NO: 15)
TTTCAGCTGGCCGATCTAAGACTGAACTCTCACCGCCGGC/iCy5/TAA
GCTATCTGCTCTTT

T3:
(SEQ ID NO: 16)
TTTGATGGAACGTTAATGAATAGTCTCCGATTGCATCCGAGATCCTAAC
TGCTGCC

T3-iCy3:
(SEQ ID NO: 17)
TTTGATGGAACGTTAAT/iCy3/AATAGTCTCCGATTGCATCCGAGATC
CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC
CTTCTCTCGTTTT

T7-Tloop:
(SEQ ID NO: 30)
GGTGACGAGTTCCGGATCACTAATTTGATAGCTTATGCCGGCAGCGTTT
TTTTTTTTTCGCAACTATTCATTAACGTTGGTACGAACG T7-2-photocage:
(SEQ ID NO: 25)
TAACCTGGCAACGGAGTGCGXTXTXTXTXTXTXCGCT

T8:
(SEQ ID NO: 22)
TTTTAGAGCACCGCTCGGTCGTTT

T9:
(SEQ ID NO: 23)
TTTCAGACGACCATCTCCTTT

Sequences of control group (polyA loop and
internal polyT strand) with locking strands

T1:
(SEQ ID NO: 13)
TTTTCGACCGAGCGGAAATTAGTGATCCGGAACTCGAGCAATGAACCTT
TT

T2:
(SEQ ID NO: 14)
TTTCAGCTGGCCGATCTAAGACTGAACTCTCACCGCCGGCATAAGCTAT
CTGCTCTTT

T2-iCy5:
(SEQ ID NO: 15)
TTTCAGCTGGCCGATCTAAGACTGAACTCTCACCGCCGGC/iCy5/TAA
GCTATCTGCTCTTT

T3:
(SEQ ID NO: 16)
TTTGATGGAACGTTAATGAATAGTCTCCGATTGCATCCGAGATCCTAAC
TGCTGCC

T3-iCy3:
(SEQ ID NO: 17)
TTTGATGGAACGTTAAT/iCy3/AATAGTCTCCGATTGCATCCGAGATC
CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC
CTTCTCTCGTTTT

T7-1-Aloop:
(SEQ ID NO: 24)
GGTGACGAGTTCCGGATCACTAATTTGATAGCTTATGCCGGCAGCGAAA
AAAAAAAAACGCAACTATTCATTAACGTTGGTACGAACG T7-2-polyT:
(SEQ ID NO: 31)
TAACCTGGCAACGGAGTGCGTTTTTTTTTTTTTCGCT T8-lock-PC:
(SEQ ID NO: 26)
CATCAGTCGAGCTGC/iSpPC/CAGAGCACCGCTCGGTCGTTT T9-lock:
(SEQ ID NO: 27)
CAGACGACCATCTGGCAGCTCGACTGATG Sequences of control group (polyA loop and
internal polyT strand) without locking
strands

T1:
(SEQ ID NO: 13)
TTTTCGACCGAGCGGAAATTAGTGATCCGGAACTCGAGCAATGAACCTT
TT

T2:
(SEQ ID NO: 14)
TTTCAGCTGGCCGATCTAAGACTGAACTCTCACCGCCGGCATAAGCTAT
CTGCTCTTT

T2-iCy5:
(SEQ ID NO: 15)
TTTCAGCTGGCCGATCTAAGACTGAACTCTCACCGCCGGC/iCy5/TAA
GCTATCTGCTCTTT

T3:
(SEQ ID NO: 16)
TTTGATGGAACGTTAATGAATAGTCTCCGATTGCATCCGAGATCCTAAC
TGCTGCC

T3-iCy3:
(SEQ ID NO: 17)
TTTGATGGAACGTTAAT/iCy3/AATAGTCTCCGATTGCATCCGAGATC
CTAACTGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC
CTTCTCTCGTTTT

T7-1-Aloop:
(SEQ ID NO: 24)
GGTGACGAGTTCCGGATCACTAATTTGATAGCTTATGCCGGCAGCGAAA
AAAAAAAAAACGCAACTATTCATTAACGTTGGTACGAACG T7-2-polyT:
(SEQ ID NO: 31)
TAACCTGGCAACGGAGTGCGTTTTTTTTTTTTCGCT

T8:
(SEQ ID NO: 22)
TTTTAGAGCACCGCTCGGTCGTTT

T9:
(SEQ ID NO: 23)
TTTCAGACGACCATCTCCTTT

Sequences of photocaged tweezers with 4 cages
T1:
(SEQ ID NO: 13)
TTTTCGACCGAGCGGAAATTAGTGATCCGGAACTCGAGCAATGAACCTT
TT

T2:
(SEQ ID NO: 14)
TTTCAGCTGGCCGATCTAAGACTGAACTCTCACCGCCGGCATAAGCTAT
CTGCTCTTT

T3:
(SEQ ID NO: 16)
TTTGATGGAACGTTAATGAATAGTCTCCGATTGCATCCGAGATCCTAAC
TGCTGCC

T4:
(SEQ ID NO: 18)
TTTTCGAGAGAAGGCTTGCCAGGTTACGTTCGTACCTCGTCTGTTT

T5:
(SEQ ID NO: 19)
TTTTGGCAGCAGTTACGGCCAGCTGATT

T6:
(SEQ ID NO: 20)
TTTTGGTTCATTGCTGAGTTCAGTCTTAGATGGATCTCGGATGCAATGC
CTTCTCTCGTTTT

T7-1-loop:
(SEQ ID NO: 32)
GGTGACGAGTTCCGGATCACTAATTTGATAGCTTATGCCGGCTGCGTAA
GACCCACAATCGCTACTATTCATTAACGTTGGTACGAACG T7-2-photocage:
(SEQ ID NO: 33)
TAACCTGGCAACGGAGAGCGAXTGXGGGXCTXACGCA

T8:
(SEQ ID NO: 22)
TTTTAGAGCACCGCTCGGTCGTTT

T9:
(SEQ ID NO: 23)
TTTCAGACGACCATCTCCTTT

Purification of DNA Oligonucleotides:

Photocaged oligonucleotides were purified by BioSynthesis using RP-HPLC. Fluorophore (Cy3/Cy5)-modified oligonucleotides and photocleavable linker modified oligonucleotides were purified by IDT using RP-HPLC. Other oligonucleotides were purified in lab using previously described method (Liu et al. 2013).

Estimation of NPOM Groups Removal Based on UV-Vis Spectra Measurement.

UV-Vis spectra of photostrand were taken before and after UV illumination. The percentage of NPOM cage molecules removal was estimated using the following calculation:

$$1 - \frac{A_{after} - A_{baseline}}{A_{before} - A_{baseline}}$$

Where Abefore, Aafter and Abaseline represents the 365 nm absorbance of photocaged strand before or after UV illumination and baseline, respectively.

DNA Nano-Tweezers Assembly:

The DNA strands constituting each DNA structure were combined in an equimolar ratio in 1×TAE-Mg$^{2+}$ buffer (40 mM Tris, 20 mM acetic acid, 2 mM EDTA and 12.5 mM magnesium acetate, pH 8.0) to reach a final concentration of 0.5 μM per strand.

Figure 5A:
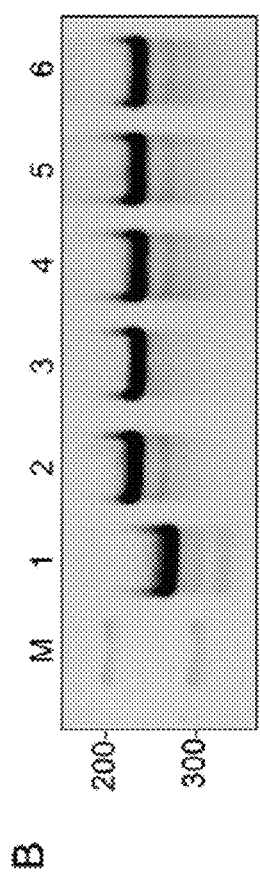
FIGS. 5A-5C show DNA sequence design and gel characterization for initially designed nano-tweezer with 4 caged residues and UV-Vis spectra of homemade photocaged DNA oligos A) Design of a nano-tweezer with random loop sequence (red) and 4 caged dT residues (X, blue) in the internal trigger strand (blue) using NPOM (SEQ ID NOs:13, 14, 16, 18, 19, 20, 22, 23, 32, and 33). B) Native PAGE gel characterization of photocaged tweezer deprotection. Lane M: ds DNA ladder (bp); lane 1: The original closed DNA nano-tweezers with random loop sequence (FIG. 2A (ii)); lane 2: The original opened DNA nano-tweezers with random loop sequence; lane 3: positive control of 4-caged nano-tweezer without NPOM residues; lane 4: photo-tweezers with 4 cages before UV deprotection; lane 5: photo-tweezers with 4 cages after UV deprotection; lane 6: re-annealed photo-tweezers after UV deprotection. C) UV-Vis spectra of 3 homemade photocaged DNA oligos (S1: XGX-ACAGTTACCGTGTGGTTGCATAGGXAXAC (SEQ ID NO:6); S2: TACCGTGTGGTTGCTGXXGXC (SEQ ID NO:7); S3: CAGACGACCATCTGGACAGAAAAAAAA XXX CXGXCC (SEQ ID NO:8); in each of S1, S2, and S3, "X" represents a photocaged thymidine residue). C1 (SEQ ID NO:35), C2 (SEQ ID NO:36), and C3 (SEQ ID NO:37) are DNA controls, of S1, S2, and S3 respectively, wherein the thymidine residues are uncaged and represent the strands produced after the exposure of the caged S1, S2, and S3 strands to UV light.
Figure 5B:
Figure 5C:
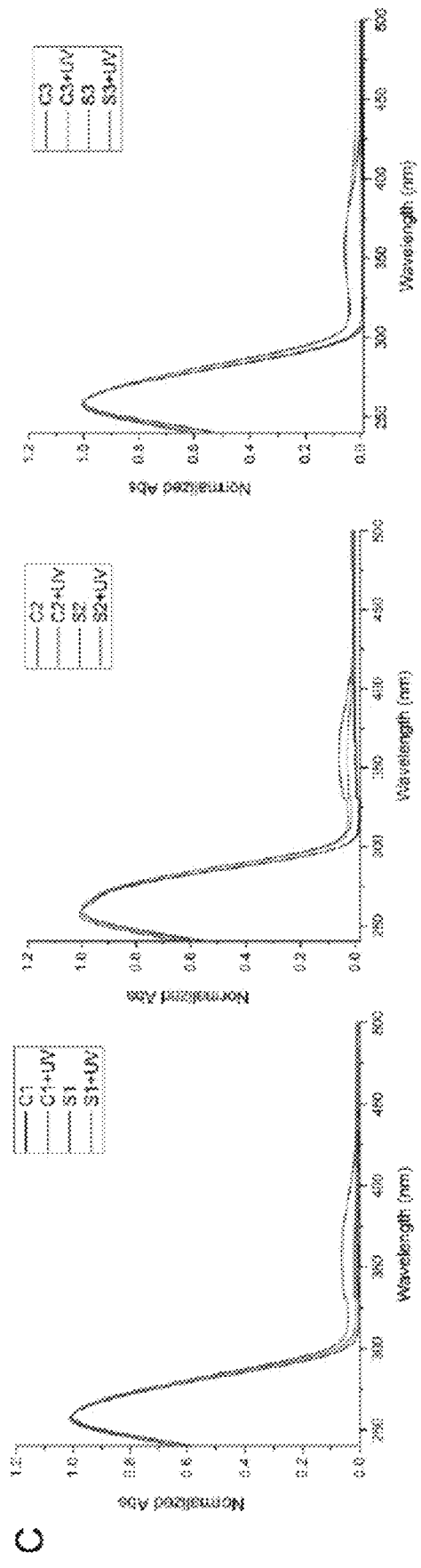
Figure 6:
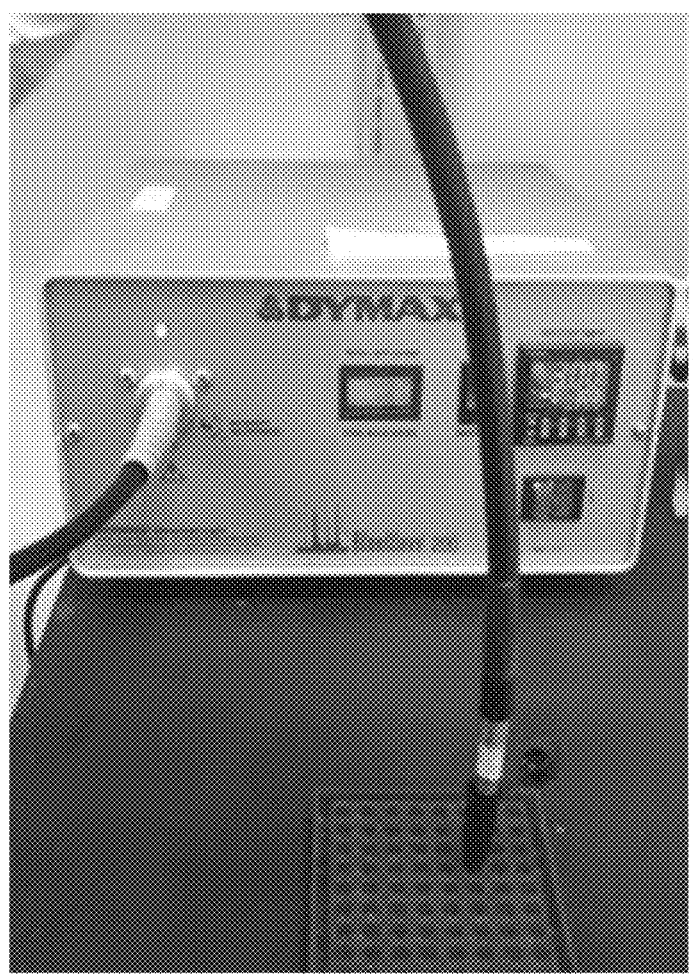
FIG. 6 is an image of a representative UV experiment setup. All experiments except cell viability assay were performed with Dymax BlueWave® 200 version 1.1 UV light-curing spot lamp system (an older version). Maximum light intensity is ~18.2 W. The end of optical fiber was placed ~1-2 cm above sample surface and a timer for 3 s exposure time was set prior to measurement.

Discussion on Photocaged Sequence Design:

Our initial photo-tweezer design used a random sequence for the hairpin loop and four photocaged residues in the internal trigger strand (FIG. 5A). However, this approach resulted in constitutively open tweezers, even prior to UV illumination (FIG. 5B). We hypothesize that this was due to the high effective molarity of the trigger (~2.7 mM) allowing binding even in the presence of four "mismatches." However, with UV-vis illumination this strand with four cages (termed S1) did undergo complete photocleavage (FIG. 5C). We next investigated adding photocaged residues closer together, including adjacent residues (strand S2), as well as increasing the number of caged residues and including three in a row (strand S3). However, by UV-Vis we observed a reduction in photocleavage for S2, and virtually no photocleavage for S3 (FIG. 5C). We hypothesized that adjacent residues might prevent efficient photocleavage due to competing mechanisms, and so settled on the final design with seven caged residues alternating with non-caged dTs. Strands S2 and S3 were made in-house on a solid-phase oligonucleotide synthesizer, using reported protocols for the phosphoramidite synthesis.

Bulk FRET Measurements

The efficiency of energy transfer (E) was determined according to the following equation:

$$E = 1 - \frac{I_{DA}}{I_D}$$

where $I_{DA}$ and $I_D$ are, respectively, the fluorescence intensities of the FRET donor (Cy3) in the presence and absence of the FRET acceptor (Cy5). All FRET calculations were performed relative to Cy3-only control samples that had also been exposed to UV to correct for any damage to the dyes, but we additionally confirmed that such damage was minimal (FIGS. 8C, 8D).

Kinetics Measurements

The kinetics for nano-tweezer opening were determined by measuring the time-dependent fluorescence change between donor and acceptor dyes using a Nanolog fluorometer (Horiba Jobin Yvon). To ensure the accuracy of the kinetics experiment, sample injection was performed with a stopped flow accessory (SFA-20, TgK Scientific) that can mix equal volumes of two samples and inject the mixtures into a cuvette for fluorescence recording in about 0.01 s (a nominal dead time <8 ms according to manufacturer's specifications). In a typical experiment, 60 μL each of the tweezer and the trigger strand (final concentrations of 60 nM for the tweezer and 60·n nM of the trigger strand, where n is the fold of trigger strand) were used for all kinetic measurements. The parameters settings for the fluorimeter were as follows: 550 nm excitation, 1 nm excitation slit, 670 nm emission, 10 nm emission slit. The signal was collected from 0 to 300 s with 0.5 s integration time and 1 s intervals. Kinetic measurements were repeated 4-6 times for each condition at 20° C. The rate constant of the reaction was obtained by fitting the data as described below.

Kinetic Model.

The opening of the photo-caged tweezer is an intramolecular reaction, and so it was analyzed as a first order reaction. For the reaction shown below, the rate constant of the forward reaction is k. As the photo-uncaging process is irreversible, the backward reaction can be neglected. The initial concentrations of the closed tweezer is ($C_0$).

$$T_{close} \overset{k}{\rightarrow} T_{open}$$

The reaction rate can be described as follows:

$$r = \frac{-d[T_{close}]}{dt} = k[T_{close}]$$

Integrating the above equation gives the following:

$$\ln([T_{close}]) = -kt + \ln(C_0)$$

$$-kt = \ln\left(\frac{[T_{close}]}{C_0}\right)$$

$$\frac{[T_{close}]}{C_0} = e^{-kt}$$

The next step is to relate the equation above to the experimental data we collected. For each kinetic curve, at time 0, after time t, and at the end of the reaction (t goes to ∞), the normalized fluorescence intensities are $I_0$, $I_t$, and $I_\infty$, respectively.

$$\frac{[T_{close}]}{C_0} = e^{-kt} = \frac{I_t - I_\infty}{I_0 - I_\infty}$$

Then, $$I_t = I_\infty + (I_0 - I_\infty)e^{-kt} \qquad (1)$$

The above equation is used to fit the normalized kinetic curve with time by using three parameters: $I_\infty$, $I_0$, and k.

The opening of the trigger strand-actuated tweezer is an intermolecular reaction, and so it was analyzed as a second order reaction. For the reaction shown below, the rate constants of the forward reaction is k. Once again, the backward reaction can be neglected because the free energy of hybridization precludes loss of the displacement strand. The initial concentrations of the closed tweezer and the trigger strand is $C_0$ and n·$C_0$, respectively, where n is the fold added of the trigger strand.

$$T_{close} + \text{Fuel} \overset{k}{\rightarrow} T_{open}$$

The reaction rate can be described as follows:

$$r = \frac{-d[T_{close}]}{dt} = k[T_{close}][\text{Fuel}] = k[T_{close}](n \cdot [T_{close}])$$

When n=1, the initial concentrations of the closed tweezer and the trigger strand are the same ($C_0$). The reaction rate can be simplified as follows:

$$r = \frac{-d[T_{close}]}{dt} = k[T_{close}][\text{Fuel}] = k[T_{close}]^2$$

Next, definite integration can be applied to the above equation to obtain the following:

$$\frac{[T_{close}]}{C_0} = \frac{1}{1 + ktC_0}$$

The next step is to relate the equation above to the experimental data we collected. For each kinetic curve, at time 0, after time t, and at the end of the reaction (t goes to ∞), the normalized fluorescence intensities are $I_0$, $I_t$, and $I_\infty$, respectively.

$$\frac{[T_{close}]}{C_0} = \frac{1}{1 + ktC_0} = \frac{I_t - I_\infty}{I_0 - I_\infty}$$

Then, $$I_t = I_\infty + \frac{I_0 - I_\infty}{1 + ktC_0}$$

The above equation is used to fit the normalized kinetic curve with time by using three parameters: $I_\infty$, $I_0$, and k.

When n is not 1, the initial concentrations of the closed tweezer and the trigger strand are different. Then, definite integration can be applied to the above equation to obtain the following:

$$\frac{-\ln([T_{close}]) + \ln(C_0)}{(n-1)C_0} - \frac{-\ln((n-1) \cdot C_0 + [T_{close}]) + \ln(n \cdot C_0)}{(n-1)C_0} = kt$$

-continued $$(n-1)C_0 \cdot kt =$$

$$\ln((n-1) \cdot C_0[T_{close}]) - \ln([T_{close}]) - \ln(n) = \ln\left(\frac{(n-1) \cdot C_0}{n \cdot [T_{close}]} + \frac{1}{n}\right)$$

$$\frac{[T_{close}]}{C_0} = \frac{n-1}{n \cdot e^{(n-1)C_0 \cdot kt} - 1}$$

The next step is to relate the equation above to the experimental data we collected. For each kinetic curve, at time 0, after time t, and at the end of the reaction (t goes to ∞), the normalized fluorescence intensities are $I_0$, $I_t$, and $I_\infty$, respectively.

$$\frac{[T_{close}]}{C_0} = \frac{n-1}{n \cdot e^{(n-1)C_0 \cdot kt} - 1} = \frac{I_t - I_\infty}{I_0 - I_\infty}$$

Then, $$I_t = I_\infty + (I_0 - I_\infty)\frac{n-1}{n \cdot e^{(n-1)C_0 \cdot kt} - 1} \qquad (2)$$

The above equation is used to fit the normalized kinetic curve with time by using three parameters: $I_\infty$, $I_0$, and k.

TABLE 1

Calculated time to reach 90% of the open FRET emission for System ii.

| Ration (trigger/tweezer) | 1 | 2 | 5 | 10 | 20 | 22 | 25 |
|---|---|---|---|---|---|---|---|
| $t_{90}$ (s) | 915 | 254 | 89 | 38 | 33 | 29 | 24 |

Computational Simulations to Determine Force Exerted by Tweezer

The DNA photo-tweezer introduced in this work can be used for a number of applications that require applying a rapid force at the nanoscale upon illumination. For example, the tweezer could be used as a nanoscale molecular machine—pulling apart two bound proteins, a ligand from its receptor, or applying a force to two different points on a protein surface—by attaching the relevant components to the ends of the tweezer arms. Thus, we were interested to determine what force this structure could apply, and over what distance.

The system uses the chemical energy—provided by the uncaged strand binding to the complementary hairpin loop—to pull apart the arms connected by a newly hybridized duplex. If duplex DNA behaved as a rigid rod, we could assume that most of the binding free energy could be used to pull apart the components bound to the tweezer arms. However, on short length scales DNA has been shown to be much more bendable than implied by a worm-like-chain (WLC) model with persistence length of 50 nm, which is typically used to describe the mechanical behavior of dsDNA (see for instance experimental results in Fields et al. 2013 and a review in Vologodskii et al. 2013). It turns out that the DNA duplex can "kink" (as illustrated in FIG. 14), thereby bending sharply at a much lower energy cost than predicted by the WLC model.

To study the range of forces that can be achieved by the tweezer system, we studied the hybridization process of the complementary strands via computer simulations using oxDNA: a coarse-grained model parametrized to capture basic structural, mechanical, and thermodynamic properties of DNA. It has an accurate representation of properties of both single-stranded and double-stranded DNA, and has been applied to a variety of DNA nano-technological systems (for example, see Doye et al. 2013 for an overview). In particular, it has been shown to reproduce DNA bending and kinking behavior as observed experimentally (Harrison et al. 2015, Harrison et al. 2015).

Figures 14A, 14B, 14C, 14D:
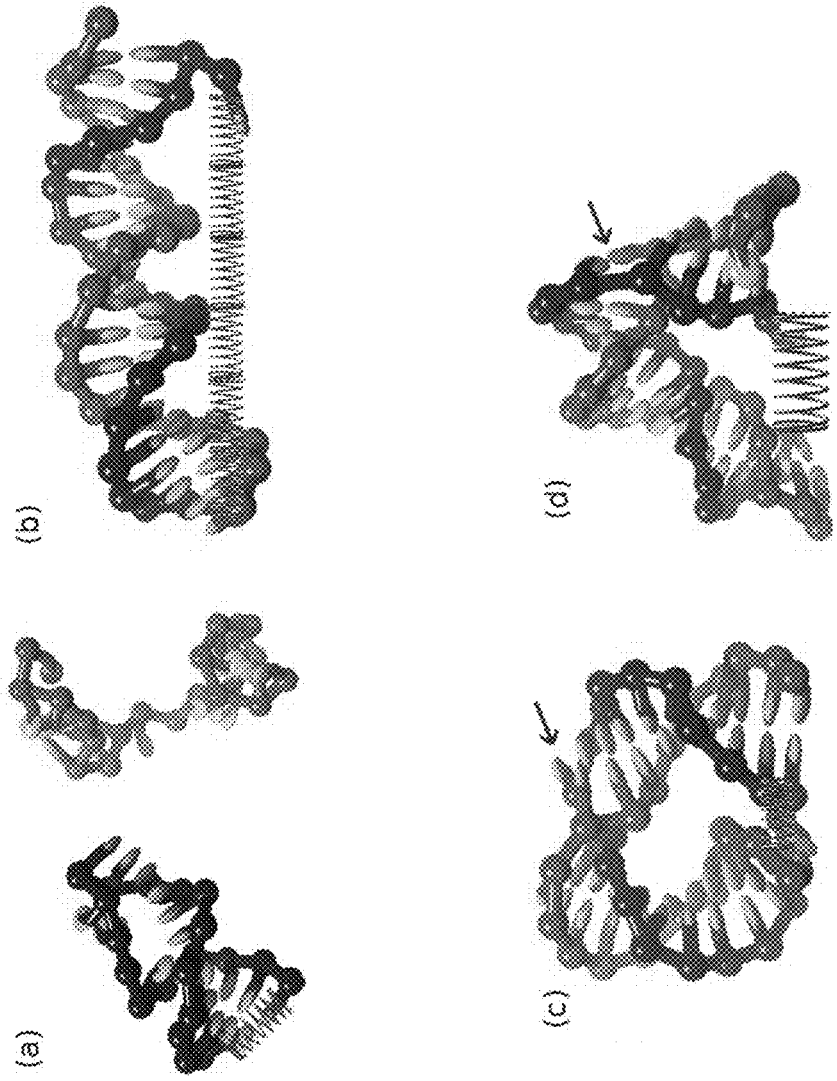
FIGS. 14A-14D shows an exemplary configuration of a simulated system for: (a) unbound strands, (b) fully formed duplex without a kink, with the choice of stiffness k=11.4 pN/nm, (c) kinked configuration of a formed duplex (with a broken base pairing interaction indicated by an arrow) for a choice of k=2240 pN/nm, (d) kinked configuration with a broken stacking interaction (indicated by an arrow) between subsequent base pairs (for k=48.63 pN/nm). The two nucleotides between which the spring potential V acts are connected by a schematic image of a spring.
Figure 15:
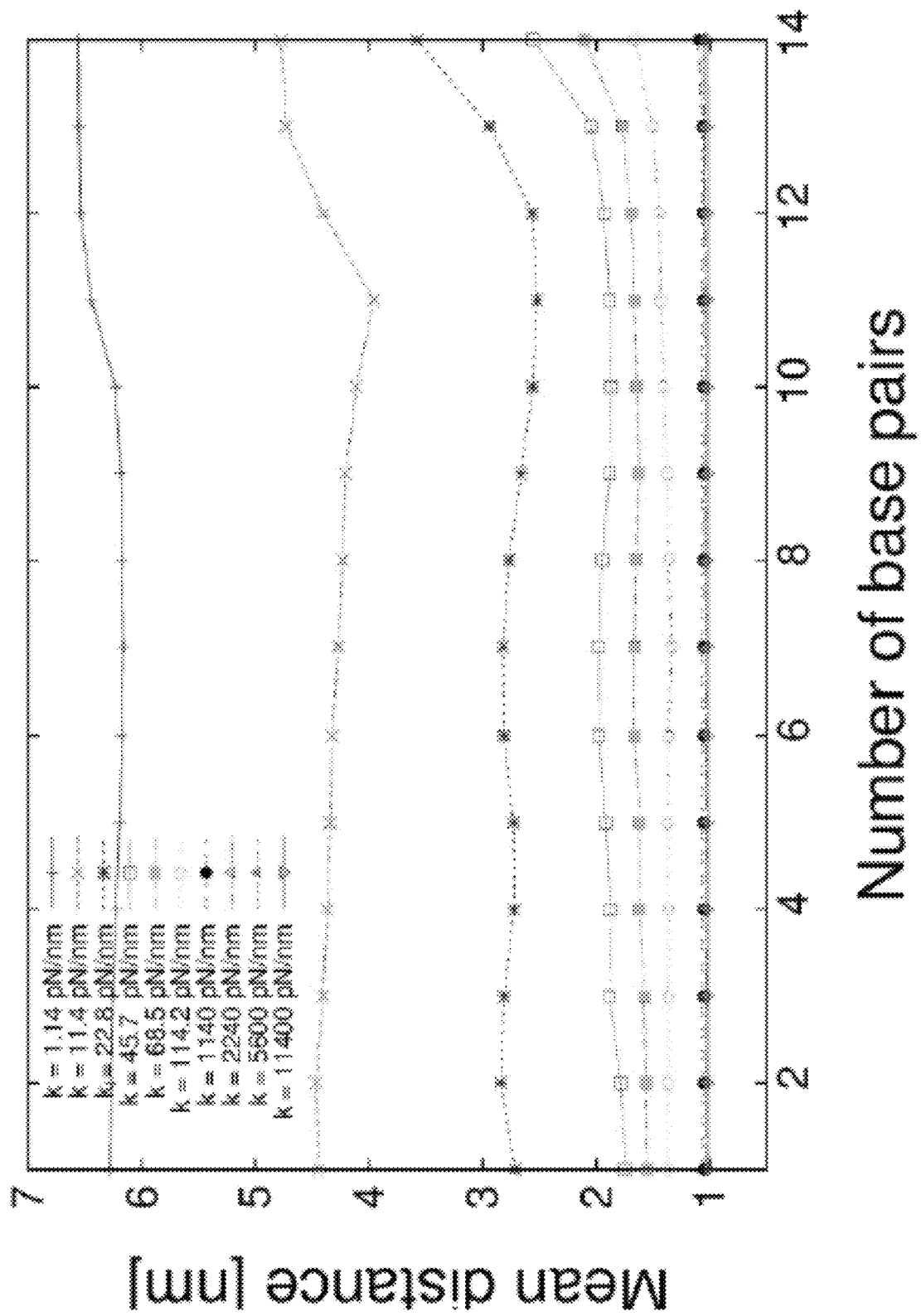
FIG. 15 shows mean distance between the bases that are bound by a spring potential as a function of the number of base pairs formed between the two complementary sequences in the simulation. As spring stiffness k gets larger, the distance gets closer to $r_0=1$ nm, the distance at which the spring potential V reaches its minimum energy.
Figure 16:
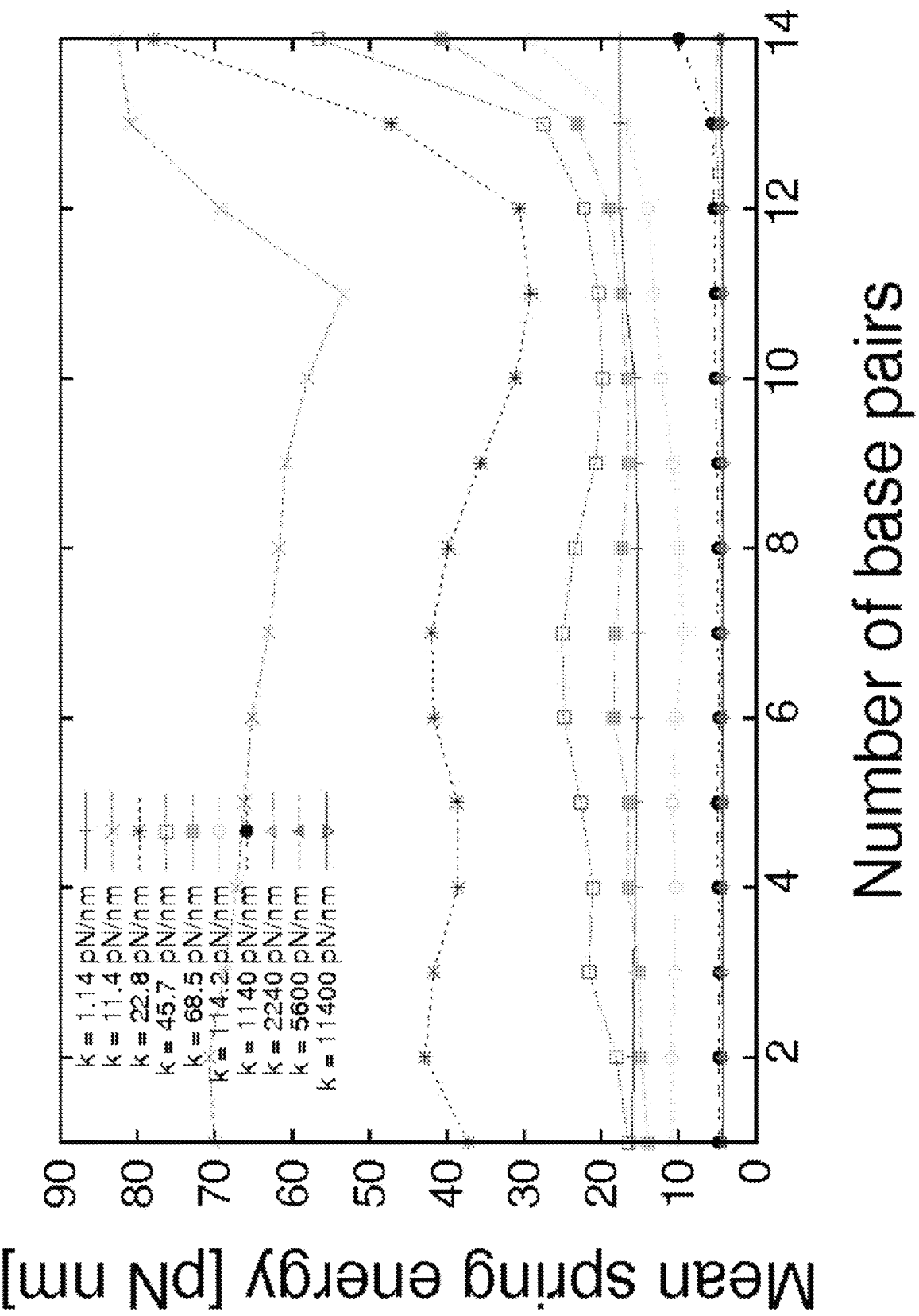
FIG. 16 shows mean energy of the spring potential V (defined in Eq. 3) as a function of the number of base pairs formed between the two complementary strands for different values of spring stiffness k. As k gets larger, the duplex prefers to kink rather than stretch the spring and hence the mean energy of the spring potential is lower for higher values of k.
Figure 17:
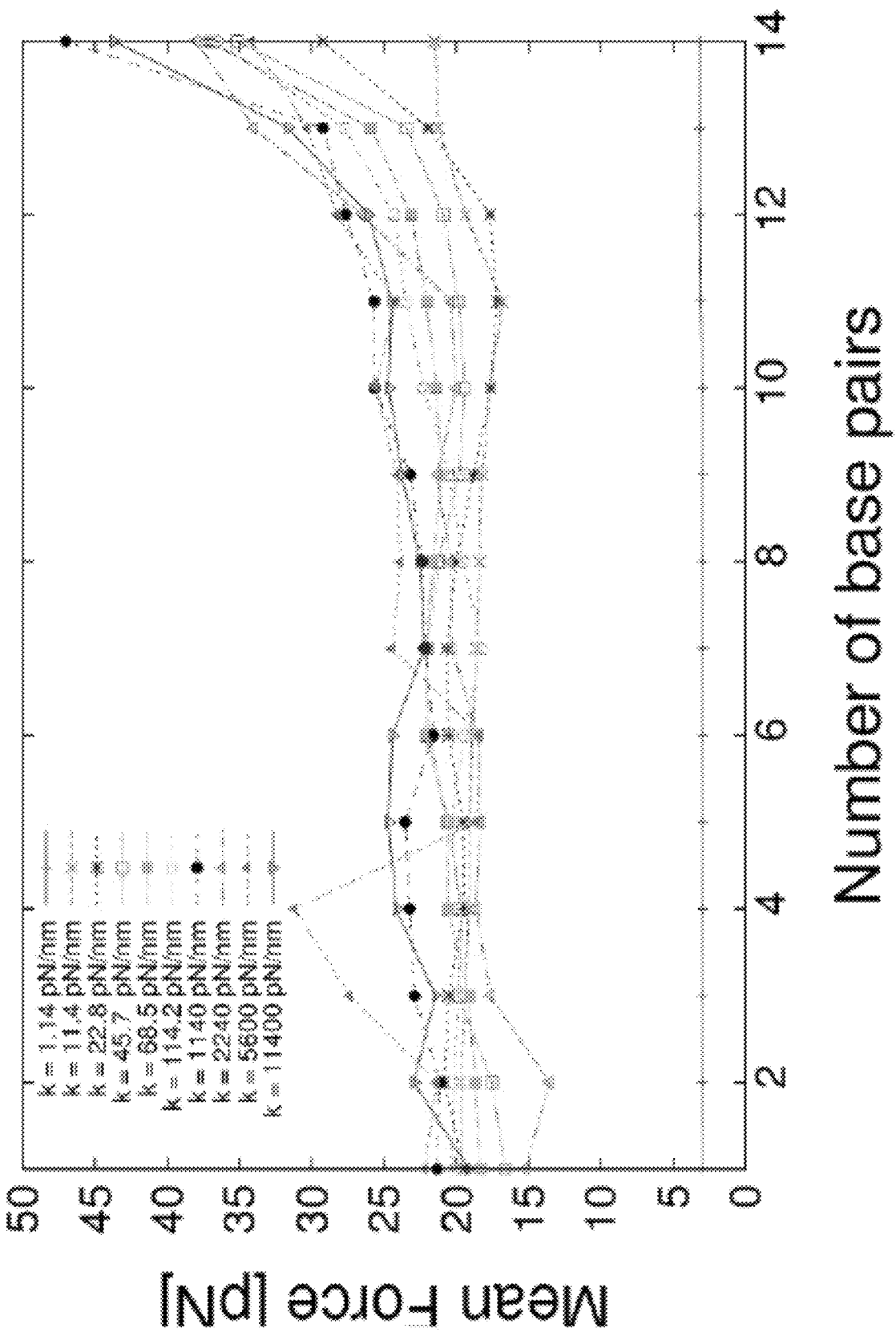
FIG. 17 shows mean force exerted on the spring connecting the two base pairs at the end of a duplex as a function of number of base pairs formed between the two complementary strands.
Figure 18:
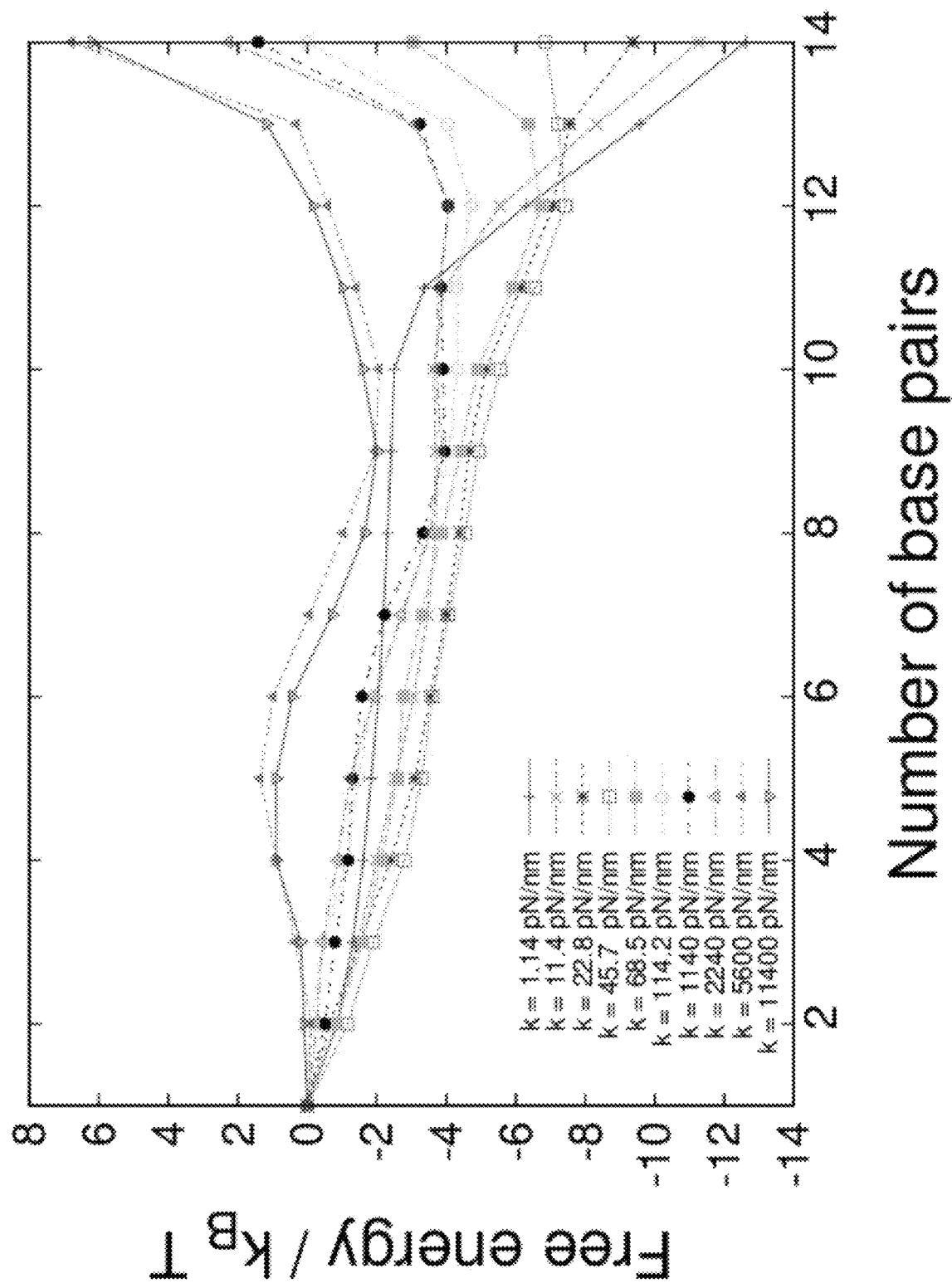
FIG. 18 shows free energy of the (partially) hybridized duplex of the two complementary strands. The probability of the system adopting a given state is proportional to exp(F/kBT), where F is the free energy of the given state. Note that as the spring stiffness k increases, the most probable hybridized state will be only a partially hybridized complex (corresponding to a minimum of the free energy as a function of the number of bases formed).
Figure 19:
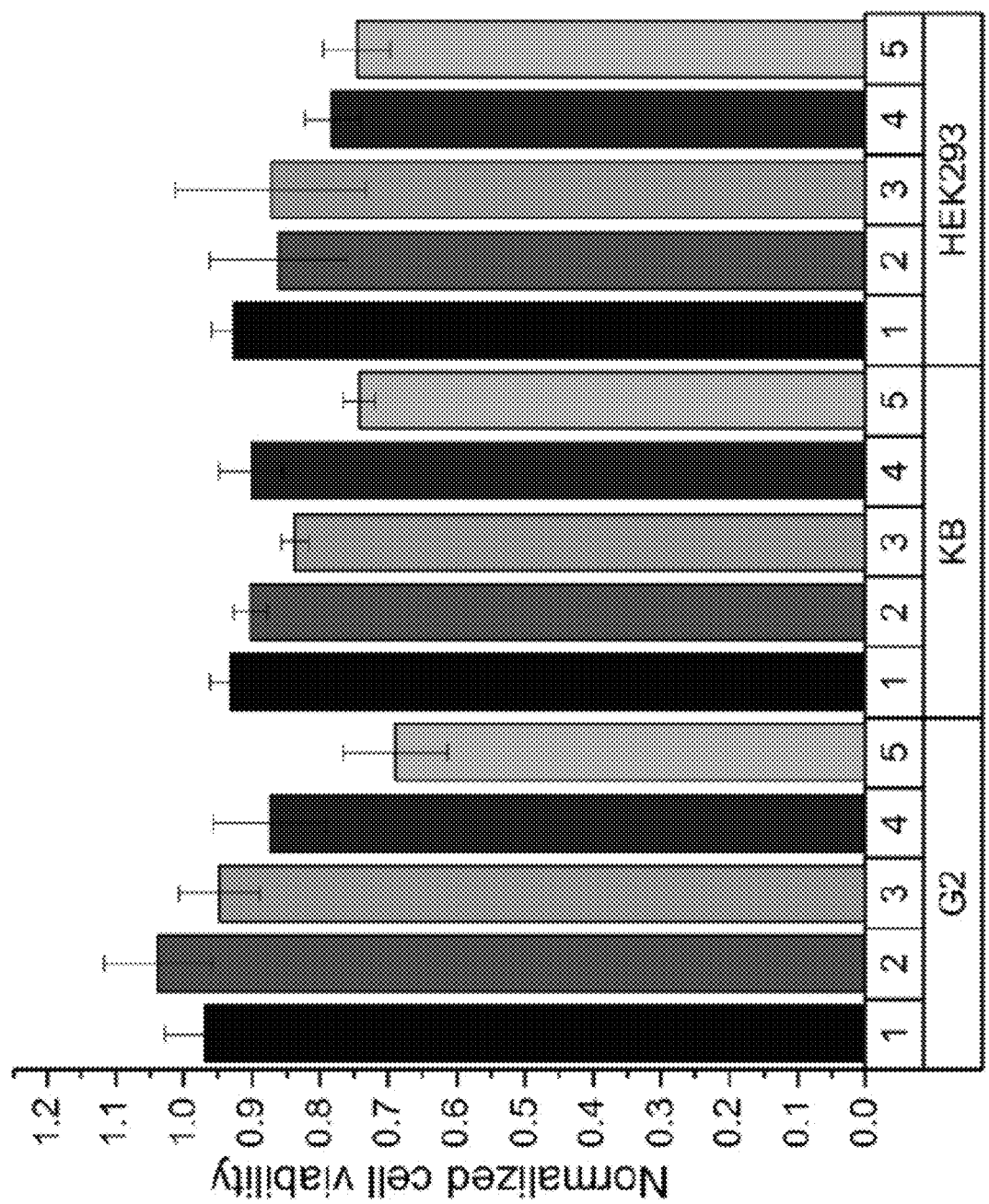
FIG. 19 shows cell viability after exposure to UV light. The cell viability was determined with respect to control cells that were not treated with UV light. 5 levels of light source intensities were used from minimum (1) to maximum (5). Level 1 intensity: 7.01 W; level 2 intensity: 9.6 W; level 3 intensity: 13.2 W; level 4 intensity: 18.4 W; level 5 intensity: 23 W. Error bars indicate standard deviation with n=10 measurements.

In oxDNA, we simulated the hybridization of two complementary strands (the same sequences used in the photo-tweezer). We introduced a harmonic potential between the first and last bases of one of these strands, defined as:

$$V(r) = \frac{k}{2}(r - r_0)^2 \qquad (3)$$

where r is the distance between the two bases, and $r_0$=1 nm corresponds to a typical distance between two hydrogen-bonded bases in the model. The typical configuration of the system when the two complementary strands are not bound is illustrated in FIG. 14A. We ran the Monte Carlo simulations to sample the hybridization of the two strands (see for example Sulc et al. 2012 for a detailed description of the hybridization sampling simulation), and measured the values of the harmonic spring potential (given by Eq. (3)) during the various stages of the hybridization, from which the corresponding force can be extracted (shown in FIG. 14). We tested a range of stiffness values k for the spring potential. When the spring energy becomes roughly comparable to, or larger, than twice the typical stacking energy between adjacent base pairs—roughly 95 pN/nm in the model—the duplex prefers to kink rather than extend the spring potential. During kinking, the spring-connected bases stay in proximity, while the duplex is bent sharply, either due to the breaking of a base pair or by breaking two stacking interactions (as shown in FIG. 14). The maximum values of the force applied by the spring potential (Eq. (3)) observed in the hybridized state in the sampling simulation was approximately 46 pN, as shown in FIG. 17. For a given energy value of V(r), the larger the stiffness k, the smaller the distance r between the spring-joined bases. This limits the maximum distance at which the tweezer would be able to pull apart for instance two interacting proteins. Note however that as the stiffness k increases, the system will prefer to form only partially formed of kinked duplex (illustrated by the free energy profile in FIG. 19), and hence we would expect the most likely state of system to be when the tweezer opens partially or does not open at all.

We note that these simulations only considered forces applied at the end bases of the hairpin. Using the full tweezer would involve applying forces at the end of the arms, potentially kinking the duplexes that comprise them. Nevertheless, our results provide an approximate value of the forces that can be exerted by opening bases of a hairpin via hybridization. The total force exerted by the tweezer could be further enhanced by combining multiple hairpin elements into a single structure, like a large DNA origami caliper (Funke et al., 2016).

Cell Viability Assay

Cells were pre-seeded in black 96-well plates with clear bottom at $3 \times 10^4$ cells per well and allowed to grow for 24 hours. Sample rows were then exposed ~2 cm under Dymax BlueWave® 200 version 3.0 UV curing spot lamp (newer model, 5 levels of light source intensities from minimum to maximum) while control rows were blocked from UV. Treated cells were allowed to grow another 24 hours before the MTT assay. On the next day, cells were washed with PBS buffer twice and 100 μL MTT reagent (5 mg/mL) was added and cells were incubated for 4 hours. After 4 hours, the MTT reagent was removed and the sample was dissolved in 150 μL of DMSO. The absorbance was measured at 550 nm. The relative cell viability was determined with respect to the control cell incubated with DMEM.

We claim:

1. A DNA nano-tweezer comprising:
   a DNA hairpin with a single-stranded loop, a first arm, and a second arm,
   wherein the distance between the first arm and the second arm is between about 3 nm and about 18 nm; and
   a DNA trigger strand complementary to the single-stranded loop and comprising at least one photocaged residue with a protecting group.

2. The DNA nano-tweezer of claim 1, wherein the single-stranded loop is a poly-A loop the trigger strand is a poly-T strand.

3. The DNA nano-tweezer of claim 1, wherein the single-stranded loop is a poly-C loop and the trigger strand is a poly-G loop.

4. The DNA nano-tweezer of claim 1, wherein the single-stranded loop and the trigger strand are selected from the group consisting of a poly-A loop, a poly-T loop, a poly-G loop, and a poly-C loop.

5. The DNA nano-tweezer of claim 1, wherein the protecting group is a 6-nitropiperonyloxymethyl protecting group.

6. The DNA nano-tweezer of claim 1, wherein the DNA nano-tweezer additionally comprises a locking strand.

7. The DNA nano-tweezer of claim 1, wherein the locking strand comprises an o-nitrobenzyl ester photocleavable backbone.

8. The DNA nano-tweezer of claim 1 additionally comprising at least one fluorescent label.

9. The DNA nano-tweezer of claim 1 additionally comprising a ligand.

10. The DNA nano-tweezer of claim 1, wherein the distance between the first arm and the second arm is between about 4 nm and about 16 nm.

11. A method of inducing a conformational change in nanostructured DNA, the method comprising the step of
    exposing the DNA nano-tweezer of claim 1 to a pulse of light, whereby the DNA nano-tweezer undergoes a conformational change from a closed conformation to an open conformation.

12. The method of claim 11, wherein the protecting group is a 6-nitropiperonyloxymethyl protecting group and the light is UV light.

13. The method of claim 11, wherein the light has a wavelength between about 300 nm and about 400 nm.

14. The method of claim 11, wherein the pulse of light is between about 1 second and about 10 seconds.

* * * * *

```
                              SEQUENCE LISTING

<160> NUMBER OF SEQ ID NOS: 37

<210> SEQ ID NO 1
<211> LENGTH: 13
<212> TYPE: DNA
<213> ORGANISM: Artificial Sequence
<220> FEATURE:
<223> OTHER INFORMATION: synthetic

<400> SEQUENCE: 1
aaaaaaaaaa aaa                                                         13

<210> SEQ ID NO 2
<211> LENGTH: 13
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: photocaged thymidine residue
<220> FEATURE:
<221> NAME/KEY: modified_base
<222> LOCATION: (3)..(3)
<223> OTHER INFORMATION: photocaged thymidine residue
<220> FEATURE:
<221> NAME/KEY: modified_base
<222> LOCATION: (5)..(5)
<223> OTHER INFORMATION: photocaged thymidine residue
<220> FEATURE:
<221> NAME/KEY: modified_base
<222> LOCATION: (7)..(7)
<223> OTHER INFORMATION: photocaged thymidine residue
<220> FEATURE:
<221> NAME/KEY: modified_base
<222> LOCATION: (9)..(9)
<223> OTHER INFORMATION: photocaged thymidine residue
<220> FEATURE:
<221> NAME/KEY: modified_base
<222> LOCATION: (11)..(11)
<223> OTHER INFORMATION: photocaged thymidine residue
<220> FEATURE:
<221> NAME/KEY: modified_base
<222> LOCATION: (13)..(13)
<223> OTHER INFORMATION: photocaged thymidine residue

<400> SEQUENCE: 2
tttttttttt ttt                                                         13

<210> SEQ ID NO 3
<211> LENGTH: 13
<212> TYPE: DNA
<213> ORGANISM: Artificial Sequence
<220> FEATURE:
<223> OTHER INFORMATION: synthetic

<400> SEQUENCE: 3
taagacccac aat                                                         13

<210> SEQ ID NO 4
<211> LENGTH: 13
<212> TYPE: DNA
<213> ORGANISM: Artificial Sequence
<220> FEATURE:
```

```
<223> OTHER INFORMATION: synthetic

<400> SEQUENCE: 4
attgtgggtc tta                                                        13

<210> SEQ ID NO 5
<211> LENGTH: 13
<212> TYPE: DNA
<213> ORGANISM: Artificial Sequence
<220> FEATURE:
<223> OTHER INFORMATION: synthetic

<400> SEQUENCE: 5
tttttttttt ttt                                                        13

<210> SEQ ID NO 6
<211> LENGTH: 32
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: photocaged thymidine residue
<220> FEATURE:
<221> NAME/KEY: modified_base
<222> LOCATION: (3)..(3)
<223> OTHER INFORMATION: photocaged thymidine residue
<220> FEATURE:
<221> NAME/KEY: modified_base
<222> LOCATION: (28)..(28)
<223> OTHER INFORMATION: photocaged thymidine residue
<220> FEATURE:
<221> NAME/KEY: modified_base
<222> LOCATION: (30)..(30)
<223> OTHER INFORMATION: photocaged thymidine residue

<400> SEQUENCE: 6
tgtacagtta ccgtgtggtt gcataggtat ac                                   32

<210> SEQ ID NO 7
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (17)..(18)
<223> OTHER INFORMATION: photocaged thymidine residue
<220> FEATURE:
<221> NAME/KEY: modified_base
<222> LOCATION: (20)..(20)
<223> OTHER INFORMATION: photocaged thymidine residue

<400> SEQUENCE: 7
taccgtgtgg ttgctgttgt c                                               21

<210> SEQ ID NO 8
<211> LENGTH: 36
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (28)..(30)
<223> OTHER INFORMATION: photocaged thymidine residue
<220> FEATURE:
<221> NAME/KEY: modified_base
```

```
<222> LOCATION: (32)..(32)
<223> OTHER INFORMATION: photocaged thymidine residue
<220> FEATURE:
<221> NAME/KEY: modified_base
<222> LOCATION: (34)..(34)
<223> OTHER INFORMATION: photocaged thymidine residue

<400> SEQUENCE: 8
cagacgacca tctggacaga aaaaaaattt ctgtcc                              36

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
tgcgtaagac ccacaatcgc t                                              21

<210> SEQ ID NO 10
<211> LENGTH: 31
<212> TYPE: DNA
<213> ORGANISM: Artificial Sequence
<220> FEATURE:
<223> OTHER INFORMATION: synthetic

<400> SEQUENCE: 10
cgtgtggttg agcgattgtg ggtcttacgc a                                   31

<210> SEQ ID NO 11
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (5)..(5)
<223> OTHER INFORMATION: photocaged thymidine residue
<220> FEATURE:
<221> NAME/KEY: modified_base
<222> LOCATION: (7)..(7)
<223> OTHER INFORMATION: photocaged thymidine residue
<220> FEATURE:
<221> NAME/KEY: modified_base
<222> LOCATION: (9)..(9)
<223> OTHER INFORMATION: photocaged thymidine residue
<220> FEATURE:
<221> NAME/KEY: modified_base
<222> LOCATION: (11)..(11)
<223> OTHER INFORMATION: photocaged thymidine residue
<220> FEATURE:
<221> NAME/KEY: modified_base
<222> LOCATION: (13)..(13)
<223> OTHER INFORMATION: photocaged thymidine residue
<220> FEATURE:
<221> NAME/KEY: modified_base
<222> LOCATION: (15)..(15)
<223> OTHER INFORMATION: photocaged thymidine residue

<400> SEQUENCE: 11
tgcgtttttt tttttttcgc t                                              21

<210> SEQ ID NO 12
<211> LENGTH: 21
<212> TYPE: DNA
<213> ORGANISM: Artificial Sequence
<220> FEATURE:
<223> OTHER INFORMATION: synthetic
```

<400> SEQUENCE: 12
agcgaaaaaa aaaaaaacgc a                                              21

<210> SEQ ID NO 13
<211> LENGTH: 51
<212> TYPE: DNA
<213> ORGANISM: Artificial Sequence
<220> FEATURE:
<223> OTHER INFORMATION: synthetic

<400> SEQUENCE: 13
ttttcgaccg agcggaaatt agtgatccgg aactcgagca atgaaccttt t             51

<210> SEQ ID NO 14
<211> LENGTH: 58
<212> TYPE: DNA
<213> ORGANISM: Artificial Sequence
<220> FEATURE:
<223> OTHER INFORMATION: synthetic

<400> SEQUENCE: 14
tttcagctgg ccgatctaag actgaactct caccgccggc ataagctatc tgctcttt     58

<210> SEQ ID NO 15
<211> LENGTH: 58
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (41)..(41)
<223> OTHER INFORMATION: Cyanine-5

<400> SEQUENCE: 15
tttcagctgg ccgatctaag actgaactct caccgccggc ntaagctatc tgctcttt     58

<210> SEQ ID NO 16
<211> LENGTH: 56
<212> TYPE: DNA
<213> ORGANISM: Artificial Sequence
<220> FEATURE:
<223> OTHER INFORMATION: synthetic

<400> SEQUENCE: 16
tttgatggaa cgttaatgaa tagtctccga ttgcatccga gatcctaact gctgcc       56

<210> SEQ ID NO 17
<211> LENGTH: 56
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Cyanine-3

<400> SEQUENCE: 17
tttgatggaa cgttaatnaa tagtctccga ttgcatccga gatcctaact gctgcc       56

<210> SEQ ID NO 18
<211> LENGTH: 46
<212> TYPE: DNA
<213> ORGANISM: Artificial Sequence
<220> FEATURE:
<223> OTHER INFORMATION: synthetic

<400> SEQUENCE: 18
ttttcgagag aaggcttgcc aggttacgtt cgtacctcgt ctgttt          46

<210> SEQ ID NO 19
<211> LENGTH: 28
<212> TYPE: DNA
<213> ORGANISM: Artificial Sequence
<220> FEATURE:
<223> OTHER INFORMATION: synthetic

<400> SEQUENCE: 19
ttttggcagc agttacggcc agctgatt                              28

<210> SEQ ID NO 20
<211> LENGTH: 62
<212> TYPE: DNA
<213> ORGANISM: Artificial Sequence
<220> FEATURE:
<223> OTHER INFORMATION: synthetic

<400> SEQUENCE: 20
ttttggttca ttgctgagtt cagtcttaga tggatctcgg atgcaatgcc ttctctcgtt    60
tt                                                                  62

<210> SEQ ID NO 21
<211> LENGTH: 105
<212> TYPE: DNA
<213> ORGANISM: Artificial Sequence
<220> FEATURE:
<223> OTHER INFORMATION: synthetic

<400> SEQUENCE: 21
ggtgacgagt tccggatcac taatttgata gcttatgccg gctgcgtaag acccacaatc    60
gctactattc attaacgttg gtacgaacgt aacctggcaa cggag                  105

<210> SEQ ID NO 22
<211> LENGTH: 24
<212> TYPE: DNA
<213> ORGANISM: Artificial Sequence
<220> FEATURE:
<223> OTHER INFORMATION: synthetic

<400> SEQUENCE: 22
ttttagagca ccgctcggtc gttt                                  24

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
tttcagacga ccatctcctt t                                     21

<210> SEQ ID NO 24
<211> LENGTH: 89
<212> TYPE: DNA
<213> ORGANISM: Artificial Sequence
<220> FEATURE:
<223> OTHER INFORMATION: synthetic

<400> SEQUENCE: 24

```
ggtgacgagt tccggatcac taatttgata gcttatgccg gcagcgaaaa aaaaaaaaac    60
gcaactattc attaacgttg gtacgaacg                                      89
```

<210> SEQ ID NO 25
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (21)..(21)
<223> OTHER INFORMATION: photocaged thymidine residue
<220> FEATURE:
<221> NAME/KEY: modified_base
<222> LOCATION: (23)..(23)
<223> OTHER INFORMATION: photocaged thymidine residue
<220> FEATURE:
<221> NAME/KEY: modified_base
<222> LOCATION: (25)..(25)
<223> OTHER INFORMATION: photocaged thymidine residue
<220> FEATURE:
<221> NAME/KEY: modified_base
<222> LOCATION: (27)..(27)
<223> OTHER INFORMATION: photocaged thymidine residue
<220> FEATURE:
<221> NAME/KEY: modified_base
<222> LOCATION: (29)..(29)
<223> OTHER INFORMATION: photocaged thymidine residue
<220> FEATURE:
<221> NAME/KEY: modified_base
<222> LOCATION: (31)..(31)
<223> OTHER INFORMATION: photocaged thymidine residue
<220> FEATURE:
<221> NAME/KEY: modified_base
<222> LOCATION: (33)..(33)
<223> OTHER INFORMATION: photocaged thymidine residue

<400> SEQUENCE: 25

```
taacctggca acggagtgcg ttttttttt tttcgct                              37
```

<210> SEQ ID NO 26
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: o-nitrobenzyl ester photocleavable backbone
      residue

<400> SEQUENCE: 26

```
catcagtcga gctgcncaga gcaccgctcg gtcgttt                             37
```

<210> SEQ ID NO 27
<211> LENGTH: 29
<212> TYPE: DNA
<213> ORGANISM: Artificial Sequence
<220> FEATURE:
<223> OTHER INFORMATION: synthetic

<400> SEQUENCE: 27

```
cagacgacca tctggcagct cgactgatg                                      29
```

<210> SEQ ID NO 28
<211> LENGTH: 37
<212> TYPE: DNA
<213> ORGANISM: Artificial Sequence
<220> FEATURE:

<223> OTHER INFORMATION: synthetic

<400> SEQUENCE: 28
taacctggca acggagtgcg aaaaaaaaaa aaacgct                                37

<210> SEQ ID NO 29
<211> LENGTH: 76
<212> TYPE: DNA
<213> ORGANISM: Artificial Sequence
<220> FEATURE:
<223> OTHER INFORMATION: synthetic

<400> SEQUENCE: 29
ggtgacgagt tccggatcac taatttgata gcttatgccg gcagcgcgca actattcatt        60
aacgttggta cgaacg                                                       76

<210> SEQ ID NO 30
<211> LENGTH: 89
<212> TYPE: DNA
<213> ORGANISM: Artificial Sequence
<220> FEATURE:
<223> OTHER INFORMATION: synthetic

<400> SEQUENCE: 30
ggtgacgagt tccggatcac taatttgata gcttatgccg gcagcgtttt tttttttttc        60
gcaactattc attaacgttg gtacgaacg                                          89

<210> SEQ ID NO 31
<211> LENGTH: 37
<212> TYPE: DNA
<213> ORGANISM: Artificial Sequence
<220> FEATURE:
<223> OTHER INFORMATION: synthetic

<400> SEQUENCE: 31
taacctggca acggagtgcg tttttttttt tttcgct                                 37

<210> SEQ ID NO 32
<211> LENGTH: 89
<212> TYPE: DNA
<213> ORGANISM: Artificial Sequence
<220> FEATURE:
<223> OTHER INFORMATION: synthetic

<400> SEQUENCE: 32
ggtgacgagt tccggatcac taatttgata gcttatgccg gctgcgtaag acccacaatc        60
gctactattc attaacgttg gtacgaacg                                          89

<210> SEQ ID NO 33
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (22)..(22)
<223> OTHER INFORMATION: photocaged thymidine residue
<220> FEATURE:
<221> NAME/KEY: modified_base
<222> LOCATION: (25)..(25)
<223> OTHER INFORMATION: photocaged thymidine residue
<220> FEATURE:
<221> NAME/KEY: modified_base
<222> LOCATION: (29)..(29)
<223> OTHER INFORMATION: photocaged thymidine residue

```
<220> FEATURE:
<221> NAME/KEY: modified_base
<222> LOCATION: (32)..(32)
<223> OTHER INFORMATION: photocaged thymidine residue

<400> SEQUENCE: 33
taacctggca acggagagcg attgtgggtc ttacgca                              37

<210> SEQ ID NO 34
<211> LENGTH: 105
<212> TYPE: DNA
<213> ORGANISM: Artificial Sequence
<220> FEATURE:
<223> OTHER INFORMATION: synthetic

<400> SEQUENCE: 34
ggtgacgagt tccggatcac taatttgata gcttatgccg gctgcgaaaa aaaaaaaaac    60
gctactattc attaacgttg gtacgaacgt aacctggcaa cggag                   105

<210> SEQ ID NO 35
<211> LENGTH: 32
<212> TYPE: DNA
<213> ORGANISM: Artificial Sequence
<220> FEATURE:
<223> OTHER INFORMATION: synthetic

<400> SEQUENCE: 35
tgtacagtta ccgtgtggtt gcataggtat ac                                  32

<210> SEQ ID NO 36
<211> LENGTH: 21
<212> TYPE: DNA
<213> ORGANISM: Artificial Sequence
<220> FEATURE:
<223> OTHER INFORMATION: synthetic

<400> SEQUENCE: 36
taccgtgtgg ttgctgttgt c                                              21

<210> SEQ ID NO 37
<211> LENGTH: 36
<212> TYPE: DNA
<213> ORGANISM: Artificial Sequence
<220> FEATURE:
<223> OTHER INFORMATION: synthetic

<400> SEQUENCE: 37
cagacgacca tctggacaga aaaaaatttt ctgtcc                              36
```